US009222134B2

(12) United States Patent
Mann

(10) Patent No.: US 9,222,134 B2
(45) Date of Patent: Dec. 29, 2015

(54) MOLECULE DETECTION SYSTEM ON A SOLID SUPPORT

(71) Applicant: ILLUMINA, INC., San Diego, CA (US)

(72) Inventor: Tobias Mann, San Diego, CA (US)

(73) Assignee: ILLUMINA, Inc., San Diego, CA (US)

( * ) Notice: Subject to any disclaimer, the term of this patent is extended or adjusted under 35 U.S.C. 154(b) by 82 days.

(21) Appl. No.: 13/919,910

(22) Filed: Jun. 17, 2013

(65) Prior Publication Data

US 2013/0281321 A1 Oct. 24, 2013

Related U.S. Application Data

(62) Division of application No. 12/885,106, filed on Sep. 17, 2010, now Pat. No. 8,483,969.

(51) Int. Cl.
*G01N 33/48* (2006.01)
*C12Q 1/68* (2006.01)
*G01N 33/50* (2006.01)
*G01N 33/543* (2006.01)
G06F 19/20 (2011.01)
G06F 19/00 (2011.01)

(52) U.S. Cl.
CPC .............. *C12Q 1/6876* (2013.01); *G01N 33/50* (2013.01); *G01N 33/543* (2013.01); *C12Q 1/6837* (2013.01); *G06F 19/20* (2013.01); *G06F 19/703* (2013.01)

(58) Field of Classification Search
CPC ...................................... G06F 19/20
USPC .......................................... 702/19
See application file for complete search history.

(56) References Cited

U.S. PATENT DOCUMENTS

| 4,469,863 | A | 9/1984 | Ts'o et al. |
|---|---|---|---|
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,599,675 | A | 2/1997 | Brenner |
| 5,602,240 | A | 2/1997 | De Mesmaeker et al. |
| 5,637,684 | A | 6/1997 | Cook et al. |
| 5,644,048 | A | 7/1997 | Yau |
| 5,750,341 | A | 5/1998 | Macevicz |
| 6,210,891 | B1 | 4/2001 | Nyren et al. |
| 6,258,568 | B1 | 7/2001 | Nyren |
| 6,274,320 | B1 | 8/2001 | Rothberg et al. |
| 7,001,792 | B2 | 2/2006 | Sauer et al. |
| 7,033,754 | B2 | 4/2006 | Chee et al. |
| 7,057,026 | B2 | 6/2006 | Barnes et al. |
| 7,060,431 | B2 | 6/2006 | Chee et al. |
| 7,115,884 | B1 | 10/2006 | Walt et al. |
| 7,226,734 | B2 | 6/2007 | Chee et al. |
| 7,244,559 | B2 | 7/2007 | Rothberg et al. |
| 7,285,384 | B2 | 10/2007 | Fan et al. |
| 7,348,181 | B2 | 3/2008 | Walt et al. |
| 7,427,673 | B2 | 9/2008 | Balasubramanian et al. |
| 7,455,971 | B2 | 11/2008 | Chee et al. |
| 7,622,294 | B2 | 11/2009 | Walt et al. |
| 2005/0100900 | A1 | 5/2005 | Kawashima et al. |
| 2005/0191698 | A1 | 9/2005 | Chee et al. |
| 2005/0214825 | A1 | 9/2005 | Stuelpnagel |
| 2006/0160081 | A1 | 7/2006 | Milton et al. |
| 2006/0188901 | A1 | 8/2006 | Barnes et al. |
| 2006/0240439 | A1 | 10/2006 | Smith et al. |
| 2006/0281109 | A1 | 12/2006 | Barr Ost et al. |
| 2007/0166705 | A1 | 7/2007 | Milton et al. |
| 2010/0136529 | A1 | 6/2010 | Shoemaker |

FOREIGN PATENT DOCUMENTS

| WO | WO 89/10977 | 11/1989 |
|---|---|---|
| WO | WO 91/06678 | 5/1991 |
| WO | WO 2005/065814 | 7/2005 |
| WO | WO 2006/064199 | 6/2006 |
| WO | WO 2007/010251 | 1/2007 |
| WO | WO 2007/010252 | 1/2007 |
| WO | WO/2007091077 | 8/2007 |
| WO | WO 2008/119046 | 10/2008 |

OTHER PUBLICATIONS

Ausubel et al., Short Protocols in Molecular Biology, fourth edition, 1999.
Bains, et al., A novel method for nucleic acid sequence determination. Journal of Theoretical Biology 135(3), 303-7 (1988).
Beaucage, et al. The Functionalization of Oligonucleotides Via Phosphoramidite Derivatives. Tetrahedron, 49:1925-1963 (1993).
Bergstrom et al. Comparison of the base pairing properties of a series of nitroazole nucleobase analogs in the oligodeoxyribonucleotide sequence 5'd(CGCXATTYGCG)-3'; Nucleic Acid Res. 25:1935 (1997).
Brill, et al., Synthesis of Oligodeoxynucleoside Phosphorodithioates via Thioamidites. J. Am. Chem. Soc., 111:2321 (1989).
Carlsson, et al., Screening for genetic mutations. Nature, 380:207 (1996).
Cockroft, S.L., Chu, J., Amorin, M. & Ghadiri, M.R. A single-molecule nanopore device detects DNA polymerase activity with single-nucleotide resolution. J. Am. Chem. Soc. 130, 818-820 (2008).
Deamer, D.W. & Akeson, M. Nanopores and nucleic acids: prospects for ultrarapid sequencing. Trends Biotechnol. 18, 147-151 (2000).
Denpcy, et al. Synthesis of a thymidyl pentamer of deoxyribonucleic guanidine and binding studies with DNA homopolynucleotides; Proc. Natl. Acad. Sci. USA, 92:6097(1995).
Drmanac, S. et al., Accurate sequencing by hybridization for DNA diagnostics and individual genomics. Nature Biotechnology 16, 54-58 (1998).
Egholm, et al., Peptide Nucleic Acids (PNA) Oligonucleotide Analogues with an Achiral Peptide Backbone. J. Am. Chem. Soc., 114:1895 (1992).
Elser et al. Searching with iterated maps. PNAS 104:418-423 (2007).
Fodor, et al., Light-directed, spatially addressable parallel chemical synthesis. Science 251(1991).
Fotin et al., Parallel thermodynamic analysis of duplexes on oligodeoxyribonucleotide microchips. Nucleic Acid Res. 26:1515 (1998).
Healy, K. Nanopore-based single-molecule DNA analysis. Nanomed. 2, 459-481 (2007).
Hong, et al., Integrated nanoliter systems. Nat. Biotechnol. 21, 1179-1183 (2003).

(Continued)

*Primary Examiner* — Jerry Lin
(74) *Attorney, Agent, or Firm* — Knobbe, Martens, Olson & Bear LLP

(57) ABSTRACT

Disclosed herein are compositions and methods used for detecting different types of molecules associated with a site on a solid support.

22 Claims, No Drawings

(56) References Cited

OTHER PUBLICATIONS

Horn et al. Oligonucleotides with Alternating Anionic and Cationic Phosphoramidate Linkages: Synthesis and Hybridization of Stereo-uniform Isomers. Tetrahedron Lett., 37:743 (1996).
Hunkapiller, T., Kaiser, R.J., Koop, B.F. & Hood, L. Large-scale and automated DNA sequence determination. Science 254, 59-67 (1991).
Gao et al. Unusual conformation of a 3'-thioformacetal linkage in a DNA duplex. J. Biomolecular NMR, 34:17 (1994).
Jenkins, et al., The Biosynthesis of Carbocyclic Nucleosides. Chem. Soc. Rev., (1995) pp. 169-176.
Jolliffe, I.T. Principal Component Analysis Series: Springer Series in Statistics, $2^{nd}$ ed., Springer, N.Y. 2002.
Kiedrowski, et al. Parabolic Growth of a Self-Replicating hexadeoxynucleotide Bearing a 3'-5'-Phosphoamidate Linkage. Angew. Chem. Intl. Ed. English, 30:423 (1991).
Korlach, J. et al. Selective aluminum passivation for targeted immobilization of single DNA polymerase molecules in zero-mode waveguide nanostructures. Proc. Natl. Acad. Sci. USA 105, 1176-1181 (2008).
Letsinger, et al., Phosphoramidate Analogs of Oligonucleotides. J. Org. Chem., 35:3800 (1970).
Letsinger, et al., Effects of pendant groups at phosphorus on binding properties of d-ApA analogues. Nucl. Acids Res., 14:3487 (1986).
Letsinger, et al., Cationic Oligonucleotides. J. Am. Chem. Soc., 110:4470 (1988).
Letsinger, et al., Hybridization of Alternating Cationic/Anionic Oligonucleotides to RNA Segments. Nucleosides & Nucleotides, 13:1597 (1994).
Levene, M.J. et al. Zero-mode waveguides for single-molecule analysis at high concentrations. Science 299,682-686 (2003).
Lipshutz, et al., Using Oligonucleotide Probe Arrays to Access Genetic Diversity. *Biotechniques* 19, 442-447 (1995).
Loakes et al., 5-Nitroindole as an universal base analogue. Nucleic Acid Res. 22:4039 (1994).
Loakes et al., 3-Nitropyrrole and 5-nitroindole as universal bases in primers for DNA sequencing and PCR. Nucleic Acid Res. 23:2361 (1995).
Loakes et al., Stability and Structure of DNA Oligonucleotides Containing Non-specific Base Analogues. J. Mol. Biol. 270:426 (1997).
Lundquist, P.M. et al. Parallel confocal detection of single molecules in real time. Opt. Lett. 33, 1026-1028 (2008).
Mag et al., Synthesis and Selective Cleavage of an Oligodeoxynucleotide Containing a Bridged Internucleotide 5'-Phosphorothioate Linkage. Nucleic Acids Res., 19:1437 (1991).
Meier, et al. Peptide Nucleic Acids (PNAs)—Unusual Properties of Nonionic Oligonucleotide Analogues. Chem. Int. Ed. Engl., 31:1008 (1992).
Mesmaeker et al., Amide Backbone Modifications for Antisense Oligonucleotides Carrying Potential Intercalating Substituents: Influence on the Thermodynamic Stability of the Corresponding Duplexes with RNA-and DNA-Complements. Bioorganic & Medicinal Chem. Lett., 4:395 (1994).
Metzker, Emerging technologies in DNA sequencing. Genome Res. 15:1767-1776 (2005).
Paegel, B.M., Blazej, R.G. & Mathies, R.A. Microfluidic devices for DNA sequencing: sample preparation and electrophoretic analysis. Curr. Opin. Biotechnol. 14, 42-50 (2003).
Pauwels, et al. Biological Activity of New 2-5A Analogues. Chemica Scripta, 26:141 (1986).
Nichols et al., A Universal Nucleoside for Use at Ambiguous Sites in DNA Primers. Nature 369:492 (1994).
Nielsen et al., PNA Hybridizes to Complementary Oligonucleotides Obeying the Watson-Crick Hydrogen-Bonding Rules. Nature, 365:566 (1993).
Ronaghi, et al., Real-time DNA sequencing using detection of pyrophosphate release. Analytical Biochemistry 242(1), 84-9 (1996).
Ronaghi, et al., A sequencing method based on real-time pyrophosphate. *Science* 281(5375)363 (1998).
Ronaghi M. "Pyrosequencing sheds light on DNA sequencing." *Genome Res.* 11(1), 3-11 (2001).
Ruparel et al. Design and synthesis of a 3'-*O*-allyl photocleavable fluorescent nucleotide as a a reversible terminator for DNA sequencing by synthesis. Proc Natl Acad Sci USA 102: 5932-7 (2005).
Sambrook et al., Molecular Cloning: A Laboratory Manual, 2d Edition, (1989).
Sanger et al., DNA Sequencing with Chain-Terminating Inhibitors. Proc. Natl. Acad. Sci. USA 74:5463-5467 (1977).
Sawai, et al., Synthesis and Properties of Oligoadenylic Acids Containing 2'-5' Phosphoramide Linkage. Chemistry Letters. 805-808 (1984).
Shendure et al., Accurate Multiplex Polony Sequencing of an Evolved Bacterial Genome. *Science* 309:1728-1732 (2005).
Soni, G.V. & Meller, A. Progress toward ultrafast DNA sequencing using solid-state nanopores. Clin. Chem. 53, 1996-2001 (2007).
Sprinzl, et al., Enzymatic Incorporation of ATP and CTP Analogues into the 3' End of tRNA. Eur. J. Biochem., 81:579 (1977).
Stevens, K., A Stochastic Process Based Approach to Phasing and Pre-phasing Parameter Estimation and Basecalling, personal communication between Kristian Stevens and Klaus Maisinger, dated May 2, 2007.
Swerdlow, H., Wu, S.L., Harke, H. & Dovichi, N. J. Capillary gel electrophoresis for DNA sequencing. J. Chromatogr. 516, 61-67 (1990).
Van Aerschot et al., An Acyclic 5-Nitroindazole Nucleoside Analogue as Ambiguous Nucleoside. Nucleic Acid Res. 23:4363 (1995).
Nealen. An As-Short-As-Possible Introduction to the Least Squares, Weighted Least Squares and Moving Least Squares Methods for Scattered Data Approximation and Interpolation. In Technical Report, TU Darmstadt (2004).
Sanghvi Y.S. and Cook, P.D., Carbohydrate Modifications in Antisense Research, Oxford University Press, Washington, D.C., (1994).
Brenner, et al. In vitro cloning of complex mixtures of DNA on microbeads: Physical separation of differentially expressed cDNAs PNAS, 971665-1670 (2000).

MOLECULE DETECTION SYSTEM ON A SOLID SUPPORT

RELATED APPLICATIONS

This application is a divisional of U.S. patent application Ser. No. 12/885,106, entitled VARIATION ANALYSIS FOR MULTIPLE TEMPLATES ON A SOLID SUPPORT, filed Sep. 17, 2010, the disclosure of which is incorporated herein by reference in its entirety.

TECHNOLOGICAL FIELD

The present technology relates to the fields of biological and molecular sciences. More particularly, the present technology relates to compositions and methods for analyzing molecules, such as nucleic acids, associated with a solid support.

BACKGROUND

Molecular sequencing, such as nucleic acid sequencing, has been used in a wide range of biological applications. For example, analysis of nucleic acid sequences has been used for identifying and classifying microorganisms, diagnosing infectious diseases, detecting and characterizing genetic abnormalities, identifying genetic changes associated with cancer, studying genetic susceptibility to disease, and measuring response to various types of treatment.

Nucleic acid sequencing methodology has evolved significantly in recent decades. Today, many sequencing methodologies require extensive sample processing prior to performing a sequencing run. As such, there is a need for methods, systems and compositions that simplify portions of the sequencing process.

SUMMARY

The present disclosure relates to methods, systems and compositions for detecting molecules. In particular, methods, systems and compositions for detecting multiple types of molecules on a solid support are described.

Some embodiments relate to methods for detecting molecules. In some embodiments, such methods comprise the steps of (a) providing a solid support comprising molecules associated with a site on the solid support such that the molecules are detected in aggregate during a detection step, wherein the site comprises at least two different types of molecules; (b) detecting a signal corresponding to the aggregate of molecules at the site; (c) estimating the fraction of different types of molecules at the site or estimating the amount of signal corresponding to different types of molecules at the site; (d) calculating the amount of signal corresponding to different types of molecules at the site using the fraction estimate, thereby obtaining a signal estimate or calculating the fraction of different types of molecules at the site using the signal estimate, thereby obtaining a fraction estimate; and (e) iteratively updating the fraction estimate and signal estimate until the estimates converge, thereby detecting molecules associated with the site.

In some embodiments of the above-described methods, the providing step further comprises providing a mixture of molecules to the solid support. In other embodiments, the providing step further comprises associating the molecules with the site. In still other embodiments, the providing step further comprises attaching the molecules at the site.

In some embodiments of the above-described methods, the estimating step is performed by guessing the fraction of different types of molecules at the site or guessing the amount of signal corresponding to different types of molecules at the site. In other embodiments, the estimating step comprises performing a principal component analysis (PCA).

In some embodiments of the above-described methods, the updating step comprises performing a numerical optimization algorithm. In some such methods, the numerical optimization algorithm is based on an iterative map search. In some such embodiments, the numerical optimization algorithm is based on Fienup's iteration map.

In some embodiments of the above-described methods, sequence data is obtained for one or more molecules. In some such methods, sequence data is obtained by a sequencing-by-synthesis process. In certain embodiments, the sequencing-by-synthesis process comprises a pyrosequencing process.

In some embodiments of the above-described methods, the solid support comprises a bead. In some other embodiments, the solid support comprises a flow-cell.

In some embodiments of the above-described methods, about 1,000 to about 10,000 molecules are associated with the site. In other embodiments, about 2,000 to about 8,000 molecules are associated with the site. In yet other embodiments, about 3,000 to about 6,000 molecules are associated with the site. In some embodiments, the molecules are attached at the sites.

In still other embodiments of the methods described herein, a site comprises about 2 to about $10^{11}$ molecules, about 2 to about $10^{10}$ molecules, about 2 to about $10^9$ molecules, about 2 to about $10^8$ molecules, about 2 to about $10^7$ molecules, about 2 to about $10^6$ molecules, about 2 to about $10^5$ molecules or about 2 to about $10^4$ molecules. In other embodiments, a site comprises about 10 to about $10^{11}$ molecules, about 10 to about $10^{10}$ molecules, about 10 to about $10^9$ molecules, about 10 to about $10^8$ molecules, about 10 to about $10^7$ molecules, about 10 to about $10^6$ molecules, about 10 to about $10^5$ molecules or about 10 to about $10^4$ molecules. In still other embodiments, the site comprises about 50 to about $10^{11}$ molecules, about 50 to about $10^{10}$ molecules, about 50 to about $10^9$ molecules, about 50 to about $10^8$ molecules, about 50 to about $10^7$ molecules, about 50 to about $10^6$ molecules, about 50 to about $10^5$ molecules or about 50 to about $10^4$ molecules. In yet other embodiments, a site comprises about 100 to about $10^{11}$ molecules, about 100 to about $10^{10}$ molecules, about 100 to about $10^9$ molecules, about 100 to about $10^8$ molecules, about 100 to about $10^7$ molecules, about 100 to about $10^6$ molecules, about 100 to about $10^5$ molecules or about 100 to about $10^4$ molecules. In any of the above-described embodiments of the methods described herein, the molecules present at a site can be detected in aggregate. In some embodiments, the molecules are associated with the site. In other embodiments, the molecules are attached at the site.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In preferred embodiments of the above-described methods, the molecules comprise nucleic acids. In some such methods, the nucleic acids are attached at the site. In some embodiments, the nucleic acids comprise a first subpopulation of nucleic acids and a second subpopulation of nucleic acids, wherein the nucleic acids of the first subpopulation each have an identical target region and the nucleic acids of the second subpopulation each have an identical region that is a variant of the target region.

In some embodiments, the nucleotide sequence of the target region of the nucleic acids of the first subpopulation has at least 1 nucleotide that is different as compared to the nucleotide sequence of the variant of the target region of the nucleic acids of the second subpopulation. In some embodiments, the nucleotide sequence of the target region of the nucleic acids of the first subpopulation has at least 3 nucleotides that are different as compared to the nucleotide sequence of the variant of the target region of the nucleic acids of the second subpopulation.

In some embodiments, a nucleotide sequence difference between the target region in the nucleic acids of the first subpopulation and the variant of the target region in the nucleic acids of the second subpopulation comprises at least one difference selected from the group consisting of a mutation, a polymorphism, an insertion, a deletion, a substitution, a simple tandem repeat polymorphism, and a single nucleotide polymorphism (SNP).

In some embodiments, the nucleic acids comprise alleles of a genetic locus from a polyploid organism. In some other embodiments, the nucleic acids comprise alternative splicing forms of a nucleic acid. In yet other embodiments, the nucleic acids comprise alleles of a genetic locus from a diploid organism.

Also described herein are molecule detection systems. The molecule detection systems can comprise a solid support comprising molecules associated with a site on the solid support such that the molecules are detected in aggregate, wherein the molecules comprise at least two different types of molecules, and a detector configured to detect the molecules associated with the site. In some embodiments, the molecules are attached at the site. In a preferred embodiment, the molecules comprise nucleic acids.

In some embodiments of the molecule detection systems described herein, a site comprises about 2 to about $10^{11}$ molecules, about 2 to about $10^{10}$ molecules, about 2 to about $10^9$ molecules, about 2 to about $10^8$ molecules, about 2 to about $10^7$ molecules, about 2 to about $10^6$ molecules, about 2 to about $10^5$ molecules, about 2 to about $10^4$ molecules. In other embodiments, a site comprises about 10 to about $10^{11}$ molecules, about 10 to about $10^{10}$ molecules, about 10 to about $10^9$ molecules, about 10 to about $10^8$ molecules, about 10 to about $10^7$ molecules, about 10 to about $10^6$ molecules, about 10 to about $10^5$ molecules, about 10 to about $10^4$ molecules. In still other embodiments, the site comprises about 50 to about $10^{11}$ molecules, about 50 to about $10^{10}$ molecules, about 50 to about $10^9$ molecules, about 50 to about $10^8$ molecules, about 50 to about $10^7$ molecules, about 50 to about $10^6$ molecules, about 50 to about $10^5$ molecules, about 50 to about $10^4$ molecules. In yet other embodiments, a site comprises about 100 to about $10^{11}$ molecules, about 100 to about $10^{10}$ molecules, about 100 to about $10^9$ molecules, about 100 to about $10^8$ molecules, about 100 to about $10^7$ molecules, about 100 to about $10^6$ molecules, about 100 to about $10^5$ molecules, about 100 to about $10^4$ molecules. In any of the above-described embodiments of the molecule detection systems described herein, the molecules present at a site can be detected in aggregate. In some embodiments, the molecules are associated with the site. In other embodiments, the molecules are attached at the site. In certain embodiments, the molecules comprise nucleic acids.

Some embodiments of the above-described molecule detection systems can further comprise a fluid handling system configured to apply fluid to the site. Other embodiments of the above-described molecule detection systems can further comprise a light source configured to provide an excitation beam to the site.

Some embodiments of the above-described molecule detection systems can further comprise a first data processing module configured to estimate the fraction of different types of molecules at the site or the amount of signal corresponding to different types of molecules at the site. In some embodiments, the first data processing module is also used for determining the variation associated with the estimate. In other embodiments, the determining step is performed using a separate data processing module.

In some embodiments of such systems, the systems can further comprise a second data processing module configured to calculate the amount of signal corresponding to different types of molecules at the site using the fraction estimate or to calculate the fraction of different types of molecules at the site using the signal estimate. In other embodiments of such systems, the systems can further comprise a third data processing module configured to iteratively update the fraction estimate and signal estimate.

In some embodiments described herein, a plurality of data processing functions can be included together in one or a few modules. In other embodiments, data processing functions can be included separately in separate modules. It will be appreciated that a first data processing module need not be separate from a second data processing module. In some embodiments, a first data processing module and a second data processing module are the same data processing module.

In some embodiments of the above-described molecule detection systems, the systems are configured to identify the nucleotide sequence of a target region of a nucleic acid.

In some embodiments of the above-described molecule detection systems, the site is a well. In some other embodiments of the above-described the molecule detection systems, the site is a bead, where the bead being present in a well of a multiwell substrate. In such systems, the well can further comprise beads having an enzyme attached thereto. In some embodiments, the enzyme comprises sulfurylase. In some embodiments, the enzyme comprises luciferase. In some embodiments, the enzyme comprises a separate sulfurylase enzyme and a separate luciferase enzyme. In some embodiments, the well further comprises beads having neither a nucleic acid nor an enzyme attached thereto.

In some embodiments of the above-described the molecule detection systems, about 1,000 to about 10,000 molecules are associated with the site. In some other embodiments, about 2,000 to about 8,000 molecules are associated with the site. In yet some other embodiments, about 3,000 to about 6,000 molecules are associated with the site. In a preferred embodiment, the molecules are attached at the site.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In some embodiments of the above-described molecule detection systems, the solid support comprises a bead. In some other embodiments, the solid support comprises a flow-cell.

Also provided herein are methods of identifying a target region of a nucleic acid. The methods can comprise (a) associating a first subpopulation of nucleic acids with a site on a solid support, wherein nucleic acids of the first subpopulation comprise an identical target region; (b) associating a second subpopulation of nucleic acids with the site on the solid support, wherein nucleic acids of the second subpopulation comprise an identical target region that is a variant of the target region of the nucleic acids of the first subpopulation; (c) detecting a signal corresponding to one or more nucleotides of the target region of first subpopulation nucleic acids and one or more nucleotides of the variant of the target region of second subpopulation nucleic acids; (d) estimating the fraction of first subpopulation nucleic acids and second subpopulation nucleic acids associated with the site or estimating the amount of signal corresponding to first subpopulation nucleic acids and second subpopulation nucleic acids associated with the site; (e) calculating the amount of signal corresponding to first subpopulation nucleic acids and second subpopulation nucleic acids associated with the site using the fraction estimate, or calculating the fraction of first subpopulation nucleic acids and second subpopulation nucleic acids associated with the site using the signal estimate; and (f) iteratively updating the fraction estimate and signal estimate until the estimates converge, thereby identifying a target region of a nucleic acid.

In some embodiments of the above-described methods, step (a) comprises attaching first subpopulation nucleic acids and second subpopulation nucleic acids to the solid support.

In some embodiments of the above-described methods, step (d) comprises performing a principal component analysis (PCA).

In some embodiments of the above-described methods, step (f) comprises performing a numerical optimization algorithm. In some such embodiments, the numerical optimization algorithm is based on iterative map search. In some other embodiments, the numerical optimization algorithm is based on Fienup's iteration map.

In some embodiments of the above-described methods, sequence data is obtained from both first and second subpopulation nucleic acids. In some such embodiments, sequence data is obtained by a sequencing-by-synthesis process. In some embodiments, the sequencing-by-synthesis process comprises a pyrosequencing process.

In some embodiments of the above-described methods, the solid support comprises a bead. In other embodiments of the above-described methods, the solid support comprises a flow-cell.

In some embodiments of the above-described methods, about 1,000 to about 10,000 nucleic acids are associated with the site. In other embodiments, about 2,000 to about 8,000 nucleic acids are associated with the site. In yet other embodiments, about 3,000 to about 6,000 nucleic acids are associated with the site. In some embodiments, the nucleic acids are attached at the sites.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In still other embodiments of the methods of identifying a target region of a nucleic acid described herein, a site comprises about 2 to about $10^{11}$ nucleic acids, about 2 to about $10^{10}$ nucleic acids, about 2 to about $10^9$ nucleic acids, about 2 to about $10^8$ nucleic acids, about 2 to about $10^7$ nucleic acids, about 2 to about $10^6$ nucleic acids, about 2 to about $10^5$ nucleic acids or about 2 to about $10^4$ nucleic acids. In other embodiments, a site comprises about 10 to about $10^{11}$ nucleic acids, about 10 to about $10^{10}$ nucleic acids, about 10 to about $10^9$ nucleic acids, about 10 to about $10^8$ nucleic acids, about 10 to about $10^7$ nucleic acids, about 10 to about $10^6$ nucleic acids, about 10 to about $10^5$ nucleic acids or about 10 to about $10^4$ nucleic acids. In still other embodiments, the site comprises about 50 to about $10^{11}$ nucleic acids, about 50 to about $10^{10}$ nucleic acids, about 50 to about $10^9$ nucleic acids, about 50 to about $10^8$ nucleic acids, about 50 to about $10^7$ nucleic acids, about 50 to about $10^6$ nucleic acids, about 50 to about $10^5$ nucleic acids or about 50 to about $10^4$ nucleic acids. In yet other embodiments, a site comprises about 100 to about $10^{11}$ nucleic acids, about 100 to about $10^{10}$ nucleic acids, about 100 to about $10^9$ nucleic acids, about 100 to about $10^8$ nucleic acids, about 100 to about $10^7$ nucleic acids, about 100 to about $10^6$ nucleic acids, about 100 to about $10^5$ nucleic acids or about 100 to about $10^4$ nucleic acids. In any of the above-described embodiments of the methods described herein, the nucleic acids present at a site can be detected in aggregate. In some embodiments, the nucleic acids are associated with the site. In other embodiments, the nucleic acids are attached at the site.

In some embodiments of the above-described methods, the nucleotide sequence of the target region of first subpopulation nucleic acids has at least 1 nucleotide that is different as compared to the nucleotide sequence of the variant of the target region of second subpopulation nucleic acids. In some other embodiments, the nucleotide sequence of the target region of first subpopulation nucleic acids has at least 3 nucleotides that are different as compared to the nucleotide sequence of the variant of the target region of second subpopulation nucleic acids.

In some embodiments of the above-described methods, a nucleotide sequence difference between the target region in first subpopulation nucleic acids of and the variant of the target region in second subpopulation nucleic acids comprises at least one difference selected from the group consisting of a mutation, a polymorphism, an insertion, a deletion, a substitution, a simple tandem repeat polymorphism, and a single nucleotide polymorphism (SNP).

In some embodiments of the above-described methods, first subpopulation nucleic acids and second subpopulation nucleic acids comprise alleles of a genetic locus from a polyploid organism. In some other embodiments, first subpopulation nucleic acids and second subpopulation nucleic acids comprise alternative splicing forms of a nucleic acid. In yet some other embodiments, first subpopulation nucleic acids and second subpopulation nucleic acids comprise alleles of a genetic locus from a diploid organism.

Also provided herein are methods for identifying a biosignature. The methods can comprise the steps of (a) providing samples obtained from a plurality of subjects, wherein the samples comprise molecules; (b) tagging molecules from the samples so as to identify the subject from which each sample originated; (c) associating molecules from the samples with a site on a solid support such that the molecules are detected in aggregate during a detection step, wherein the site comprises at least two different types of molecules; (d) obtaining a biosignature for molecules associated with the site by: i) detecting a signal corresponding to the aggregate of the molecules at the site, ii) estimating the fraction of different types of molecules at the site or the amount of signal corresponding to different types of molecules at the site, iii) calculating the amount of signal corresponding to different types of molecules at the site using the fraction estimate, or calculating the fraction of different types of molecules at the site using the signal estimate, and iv) iteratively updating the fraction estimate and signal estimate until the estimates converge, thereby obtaining a biosignature for molecules at the site; and (e) comparing the biosignature obtained in step (d) to a reference biosignature, thereby identifying the biosignature. In a preferred embodiment, the molecules are attached at the site.

In some embodiments of the above-described methods, about 1,000 to about 10,000 molecules are associated with the site. In other embodiments, about 2,000 to about 8,000 molecules are associated with the site. In yet other embodiments, about 3,000 to about 6,000 molecules are associated with the site. In some embodiments, the molecules are attached at the sites.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In still other embodiments of the methods described herein, a site comprises about 2 to about $10^{11}$ molecules, about 2 to about $10^{10}$ molecules, about 2 to about $10^9$ molecules, about 2 to about $10^8$ molecules, about 2 to about $10^7$ molecules, about 2 to about $10^6$ molecules, about 2 to about $10^5$ molecules or about 2 to about $10^4$ molecules. In other embodiments, a site comprises about 10 to about $10^{11}$ molecules, about 10 to about $10^{10}$ molecules, about 10 to about $10^9$ molecules, about 10 to about $10^8$ molecules, about 10 to about $10^7$ molecules, about 10 to about $10^6$ molecules, about 10 to about $10^5$ molecules or about 10 to about $10^4$ molecules. In still other embodiments, the site comprises about 50 to about $10^{11}$ molecules, about 50 to about $10^{10}$ molecules, about 50 to about $10^9$ molecules, about 50 to about $10^8$ molecules, about 50 to about $10^7$ molecules, about 50 to about $10^6$ molecules, about 50 to about $10^5$ molecules or about 50 to about $10^4$ molecules. In yet other embodiments, a site comprises about 100 to about $10^{11}$ molecules, about 100 to about $10^{10}$ molecules, about 100 to about $10^9$ molecules, about 100 to about $10^8$ molecules, about 100 to about $10^7$ molecules, about 100 to about $10^6$ molecules, about 100 to about $10^5$ molecules or about 100 to about $10^4$ molecules. In any of the above-described embodiments of the methods described herein, the molecules present at a site can be detected in aggregate. In some embodiments, the molecules are associated with the site. In other embodiments, the molecules are attached at the site.

In a preferred embodiment of the above-described methods, the molecules comprise nucleic acids. In some such embodiments, the nucleic acids comprise a marker from a pathogen. In certain embodiments, the pathogen comprises a pathogen selected from the group consisting of a virus, a bacterium and a eukaryotic cell. In some embodiments, the eukaryotic cell can be a cancer cell.

In some embodiments of the above-described methods, the sample comprises an abnormal cell type.

In some embodiments of the above-described methods, the sample comprises a mixture of eukaryotic cell types, a mixture of microorganisms or a mixture of both eukaryotic cell types and microorganisms.

In some embodiments of the above-described methods, the subject is a living material or organism. In other embodiments, the subject is not living material.

In some embodiments of the above-described methods, the sample comprises human flora. In some such embodiments, the human flora is selected from the group consisting of skin flora, nasal flora, gut flora, vaginal flora, and oral cavity flora.

In some embodiments of the above-described methods, the sample is obtained from a cancer patient.

Also described herein is a solid support including a population of nucleic acids associated with a site on the solid support such that nucleic acids of the population of nucleic acids are detected in aggregate, the population of nucleic acids comprising a first subpopulation and a second subpopulation, wherein nucleic acids of the first subpopulation comprise an identical target region and nucleic acids of the second subpopulation comprise an identical region that is a variant of the target region.

In embodiments of the above-described solid supports, about 1,000 to about 10,000 nucleic acids are associated with the site. In some other such embodiments, about 2,000 to about 8,000 nucleic acids are associated with the site. In yet other such embodiments, about 3,000 to about 6,000 nucleic acids are associated with the site. In some embodiments of the above-described solid support, the nucleic acids are attached at the site.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In other embodiments of the above-described solid support, a site comprises about 2 to about $10^{11}$ nucleic acids, about 2 to about $10^{10}$ nucleic acids, about 2 to about $10^9$ nucleic acids, about 2 to about $10^8$ nucleic acids, about 2 to about $10^7$ nucleic acids, about 2 to about $10^6$ nucleic acids, about 2 to about $10^5$ nucleic acids or about 2 to about $10^4$ nucleic acids. In other embodiments, a site comprises about 10 to about $10^{11}$ nucleic acids, about 10 to about $10^{10}$ nucleic acids, about 10 to about $10^9$ nucleic acids, about 10 to about $10^8$ nucleic acids, about 10 to about $10^7$ nucleic acids, about 10 to about $10^6$ nucleic acids, about 10 to about $10^5$ nucleic acids or about 10 to about $10^4$ nucleic acids. In still other embodiments, the site comprises about 50 to about $10^{11}$ nucleic acids, about 50 to about $10^{10}$ nucleic acids, about 50 to about $10^9$ nucleic acids, about 50 to about $10^8$ nucleic acids, about 50 to about $10^7$ nucleic acids, about 50 to about $10^6$ nucleic acids, about 50 to about $10^5$ nucleic acids or about 50 to about $10^4$ nucleic acids. In yet other embodiments, a site comprises about 100 to about $10^{11}$ nucleic acids, about 100 to about $10^{10}$ nucleic acids, about 100 to about $10^9$ nucleic acids, about 100 to about $10^8$ nucleic acids, about 100 to about $10^7$ nucleic acids, about 100 to about $10^6$ nucleic acids, about 100 to about $10^5$ nucleic acids or about 100 to about $10^4$ nucleic acids. In any of the above-described embodiments of the solid supports described herein, the nucleic acids present at a site can be detected in aggregate. In some embodiments, the nucleic acids are associated with the site. In other embodiments, the nucleic acids are attached at the site.

In some embodiments of the above-described solid support, a nucleotide sequence difference between the target region in first subpopulation nucleic acids and the variant of the target region in second subpopulation nucleic acids comprises at least one difference selected from the group consisting of a mutation, a polymorphism, an insertion, a deletion, a substitution, a simple tandem repeat polymorphism, and a single nucleotide polymorphism (SNP).

In some embodiments of the above-described solid support, the population of nucleic acids comprises alleles of a genetic locus from a polyploid organism. In other embodiments, the population of nucleic acids comprises alternative splicing forms of a nucleic acid. In yet other embodiments, the population of nucleic acids comprises alleles of a genetic locus from a diploid organism.

Also described herein are mixtures of beads comprising a plurality of beads. In some embodiments, each bead of the plurality of beads comprises a first subpopulation and a second subpopulation of nucleic acids, wherein the first subpopulation and the second subpopulation of nucleic acids are associated with the bead such that they are detected in aggregate. In a preferred embodiment, the nucleic acids of the first subpopulation each comprise an identical target region and the nucleic acids of the second subpopulation each comprise an identical region that is a variant of the target region.

In some embodiments of the above-described mixture of beads, the nucleic acids are attached to each bead of the plurality of beads.

In some embodiments, the mixture of beads is distributed on the substrate. In other embodiments, the plurality of beads having beads comprising both the first subpopulation and a second subpopulation of nucleic acids is distributed on a substrate. In some embodiments, the distribution of beads on the substrate is a random distribution. In other embodiments, the substrate comprises wells and the beads are distributed in the wells. In yet other embodiments, wells of the substrate further comprise beads having an enzyme attached thereto. In preferred embodiments, the enzyme can comprise sulfurylase, luciferase or a combination of sulfurylase and luciferase. In some embodiments, wells of the substrate further comprise beads having neither a nucleic acid nor enzyme attached thereto.

Also provided herein are beads comprising a first subpopulation of capture nucleic acids having a competitor molecule hybridized thereto and a second subpopulation of capture nucleic acids comprising a region that permits hybridization of a complementary molecule.

Also provided herein are beads comprising capture nucleic acids hybridized with an amplified nucleic acid comprising a degenerate tag, the degenerate tag being hybridized to a capture nucleic acid. In some embodiments, the bead is present in a channel of a substrate. In other embodiments, the bead is present in a well of a multiwell substrate. In a preferred embodiment, the well is configured to hold a single bead having the amplified nucleic acids hybridized thereto.

In embodiments of the above-described beads or mixtures of beads, about 1,000 to about 10,000 nucleic acids are associated with the bead. In some other such embodiments, about 2,000 to about 8,000 nucleic acids are associated with the bead. In yet other such embodiments, about 3,000 to about 6,000 nucleic acids are associated with the bead. In some embodiments of the above-described beads or mixtures of beads, the nucleic acids are attached at the bead.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In other embodiments of the above-described beads or mixtures of beads, a bead comprises about 2 to about $10^{11}$ nucleic acids, about 2 to about $10^{10}$ nucleic acids, about 2 to about $10^9$ nucleic acids, about 2 to about $10^8$ nucleic acids, about 2 to about $10^7$ nucleic acids, about 2 to about $10^6$ nucleic acids, about 2 to about $10^5$ nucleic acids or about 2 to about $10^4$ nucleic acids. In other embodiments, a bead comprises about 10 to about $10^{11}$ nucleic acids, about 10 to about $10^{10}$ nucleic acids, about 10 to about $10^9$ nucleic acids, about 10 to about $10^8$ nucleic acids, about 10 to about $10^7$ nucleic acids, about 10 to about $10^6$ nucleic acids, about 10 to about $10^5$ nucleic acids or about 10 to about $10^4$ nucleic acids. In still other embodiments, the bead comprises about 50 to about $10^{11}$ nucleic acids, about 50 to about $10^{10}$ nucleic acids, about 50 to about $10^9$ nucleic acids, about 50 to about $10^8$ nucleic acids, about 50 to about $10^7$ nucleic acids, about 50 to about $10^6$ nucleic acids, about 50 to about $10^5$ nucleic acids or about 50 to about $10^4$ nucleic acids. In yet other embodiments, a bead comprises about 100 to about $10^{11}$ nucleic acids, about 100 to about $10^{10}$ nucleic acids, about 100 to about $10^9$ nucleic acids, about 100 to about $10^8$ nucleic acids, about 100 to about $10^7$ nucleic acids, about 100 to about $10^6$ nucleic acids, about 100 to about $10^5$ nucleic acids or about 100 to about $10^4$ nucleic acids. In any of the above-described embodiments of the beads or mixtures of beads described herein, the nucleic acids present at a bead can be detected in aggregate. In some embodiments, the nucleic acids are associated with the bead. In other embodiments, the nucleic acids are attached at the bead.

Additional embodiments can be found as set forth in the numbered paragraphs below.

1. A method of detecting molecules, said method comprising the steps of (a) providing a solid support comprising molecules associated with a site on the solid support such that the molecules are detected in aggregate during a detection step, wherein the site comprises at least two different types of molecules; (b) detecting a signal corresponding to the aggregate of molecules at the site; (c) estimating the fraction of different types of molecules at the site or estimating the amount of signal corresponding to different types of molecules at the site; (d) calculating the amount of signal corresponding to different types of molecules at the site using the fraction estimate, thereby obtaining a signal estimate or calculating the fraction of different types of molecules at the site using the signal estimate, thereby obtaining a fraction estimate; and (e) iteratively updating the fraction estimate and signal estimate until the estimates converge, thereby detecting molecules associated with the site.

2. The method of paragraph 1, wherein the providing step further comprises providing a mixture of molecules to said solid support.

3. The method of paragraph 1, wherein the providing step further comprises attaching the molecules at the site.

4. The method of paragraph 1, wherein the estimating step is performed by guessing the fraction of different types of molecules at the site or guessing the amount of signal corresponding to different types of molecules at the site.

5. The method of paragraph 1, wherein the providing step further comprises associating the molecules with the site.

6. The method of paragraph 1, wherein the estimating step comprises performing a principal component analysis (PCA).

7. The method of paragraph 1, wherein the updating step comprises performing a numerical optimization algorithm.

8. The method of paragraph 7, wherein the numerical optimization algorithm is based on an iterative map search.

9. The method of paragraph 8, wherein the numerical optimization algorithm is based on Fienup's iteration map.

10. The method of paragraph 1, wherein sequence data is obtained for one or more molecules.

11. The method of paragraph 10, wherein sequence data is obtained by a sequencing-by-synthesis process.

12. The method of paragraph 11, wherein the sequencing-by-synthesis process comprises a pyrosequencing process.

13. The method of paragraph 1, wherein the solid support comprises a bead.

14. The method of paragraph 1, wherein the solid support comprises a flow-cell.

15. The method of paragraph 1, wherein about 1,000 to about 10,000 molecules are associated with the site.

16. The method of paragraph 1, wherein about 2,000 to about 8,000 molecules are associated with the site.

17. The method of paragraph 1, wherein about 3,000 to about 6,000 molecules are associated with the site.

18. The method of paragraph 1, wherein the molecules comprise nucleic acids.

19. The method of paragraph 18, wherein said nucleic acids are attached at the site.

20. The method of paragraph 18, wherein the nucleic acids comprise a first subpopulation of nucleic acids and a second subpopulation of nucleic acids, said nucleic acids of the first subpopulation each having an identical target region and the nucleic acids of the second subpopulation each having an identical region that is a variant of the target region.

21. The method of paragraph 18, wherein the nucleotide sequence of said target region of the nucleic acids of the first subpopulation has at least 1 nucleotide that is different as compared to the nucleotide sequence of said variant of the target region of the nucleic acids of the second subpopulation.

22. The method of paragraph 18, wherein the nucleotide sequence of said target region of the nucleic acids of the first subpopulation has at least 3 nucleotides that are different as compared to the nucleotide sequence of said variant of the target region of the nucleic acids of the second subpopulation.

23. The method of paragraph 18, wherein a nucleotide sequence difference between the target region in the nucleic acids of the first subpopulation and the variant of the target region in the nucleic acids of the second subpopulation comprises at least one difference selected from the group consisting of a mutation, a polymorphism, an insertion, a deletion, a substitution, a simple tandem repeat polymorphism, and a single nucleotide polymorphism (SNP).

24. The method of paragraph 18, wherein the nucleic acids comprise alleles of a genetic locus from a polyploid organism.

25. The method of paragraph 18, wherein the nucleic acids comprise alternative splicing forms of a nucleic acid.

26. The method of paragraph 18, the nucleic acids comprises alleles of a genetic locus from a diploid organism.

27. A molecule detection system comprising a solid support comprising molecules associated with a site on the solid support such that the molecules are detected in aggregate, wherein the molecules comprise at least two different types of molecules; and a detector configured to detect said molecules associated with said site.

28. The system of paragraph 27, wherein the molecule detection system further comprises a fluid handling system configured to apply fluid to said site.

29. The system of paragraph 27, wherein the molecule detection system further comprises a light source configured to provide an excitation beam to said site.

30. The system of paragraph 27, wherein the molecule detection system further comprises a first data processing module configured to estimate the fraction of different types of molecules at the site or the amount of signal corresponding to different types of molecules at the site.

31. The system of paragraph 30, wherein the molecule detection system further comprises a second data processing module configured to calculate the amount of signal corresponding to different types of molecules at the site using the fraction estimate or to calculate the fraction of different types of molecules at the site using the signal estimate.

32. The system of paragraph 31, wherein the molecule detection system further comprises a third data processing module configured to iteratively update the fraction estimate and signal estimate.

33. The system of paragraph 27, wherein the molecule detection system is configured to identify the nucleotide sequence of a target region of a nucleic acid.

34. The system of paragraph 27, wherein the site is a well.

35. The system of paragraph 27, wherein the site is a bead, said bead being present in a well of a multiwell substrate.

36. The system of paragraph 35, wherein the well further comprises beads having an enzyme attached thereto.

37. The system of paragraph 36, wherein said enzyme comprises sulfurylase.

38. The system of paragraph 36, wherein said enzyme comprises luciferase.

39. The system of paragraph 36, wherein said enzyme comprises a separate sulfurylase enzyme and a separate luciferase enzyme.

40. The system of paragraph 35, wherein the well further comprises beads having neither a nucleic acid nor an enzyme attached thereto.

41. The system of paragraph 27, wherein the molecules are attached at the site.

42. The system of paragraph 27, wherein about 1,000 to about 10,000 molecules are associated with the site.

43. The system of paragraph 27, wherein about 2,000 to about 8,000 molecules are associated with the site.

44. The system of paragraph 27, wherein about 3,000 to about 6,000 molecules are associated with the site.

45. The system of paragraph 27, wherein the molecules comprise nucleic acids.

46. The system of paragraph 27, wherein the solid support comprises a bead.

47. The system of paragraph 27, wherein the solid support comprises a flow-cell.

48. A method of identifying a target region of a nucleic acid, said method comprising (a) associating a first subpopulation of nucleic acids with a site on a solid support, wherein, nucleic acids of said first subpopulation comprise an identical target region; (b) associating a second subpopulation of nucleic acids with the site on the solid support, wherein nucleic acids of said second subpopulation comprise an identical target region that is a variant of the target region of the nucleic acids of said first subpopulation; (c) detecting a signal corresponding to one or more nucleotides of the target region of first subpopulation nucleic acids and one or more nucleotides of the variant of the target region of second subpopulation nucleic acids; (d) estimating the fraction of first subpopulation nucleic acids and second subpopulation nucleic acids associated with the site or estimating the amount of signal corresponding to first subpopulation nucleic acids and second subpopulation nucleic acids associated with the site; (e) calculating the amount of signal corresponding to first subpopulation nucleic acids and second subpopulation nucleic acids associated with the site using the fraction estimate, or calculating the fraction of first subpopulation nucleic acids and second subpopulation nucleic acids associated with the site using the signal estimate; and (f) iteratively updating the fraction estimate and signal estimate until the estimates converge, thereby identifying a target region of a nucleic acid.

49. The method of paragraph 48, wherein step (a) comprises attaching first subpopulation nucleic acids and second subpopulation nucleic acids to the solid support.

50. The method of paragraph 48, wherein step (d) comprises performing a principal component analysis (PCA).

51. The method of paragraph 48, wherein step (f) comprises performing a numerical optimization algorithm.

52. The method of paragraph 51, wherein the numerical optimization algorithm is based on iterative map search.

53. The method of paragraph 52, wherein the numerical optimization algorithm is based on Fienup's iteration map.

54. The method of paragraph 48, wherein sequence data is obtained from both first and second subpopulation nucleic acids.

55. The method of paragraph 54, wherein sequence data is obtained by a sequencing-by-synthesis process.

56. The method of paragraph 55, wherein the sequencing-by-synthesis process comprises a pyrosequencing process.

57. The method of paragraph 48, wherein the solid support comprises a bead.

58. The method of paragraph 48, wherein the solid support comprises a flow-cell.

59. The method of paragraph 48, wherein about 1,000 to about 10,000 nucleic acids are associated with the site.

60. The method of paragraph 48, wherein about 2,000 to about 8,000 nucleic acids are associated with the site.

61. The method of paragraph 48, wherein about 3,000 to about 6,000 nucleic acids are associated with the site.

62. The method of paragraph 48, wherein the nucleotide sequence of said target region of first subpopulation nucleic acids has at least 1 nucleotide that is different as compared to the nucleotide sequence of said variant of the target region of second subpopulation nucleic acids.

63. The method of paragraph 48, wherein the nucleotide sequence of said target region of first subpopulation nucleic acids has at least 3 nucleotides that are different as compared to the nucleotide sequence of said variant of the target region of second subpopulation nucleic acids.

64. The method of paragraph 48, wherein a nucleotide sequence difference between the target region in first subpopulation nucleic acids of and the variant of the target region in second subpopulation nucleic acids comprises at least one difference selected from the group consisting of a mutation, a polymorphism, an insertion, a deletion, a substitution, a simple tandem repeat polymorphism, and a single nucleotide polymorphism (SNP).

65. The method of paragraph 48, wherein first subpopulation nucleic acids and second subpopulation nucleic acids comprise alleles of a genetic locus from a polyploid organism.

66. The method of paragraph 48, wherein first subpopulation nucleic acids and second subpopulation nucleic acids comprise alternative splicing forms of a nucleic acid.

67. The method of paragraph 48, wherein first subpopulation nucleic acids and second subpopulation nucleic acids comprise alleles of a genetic locus from a diploid organism.

68. A method for identifying a biosignature, said method comprising the steps of (a) providing samples obtained from a plurality of subjects, wherein the samples comprise molecules; (b) tagging molecules from the samples so as to identify the subject from which each sample originated; (c) associating molecules from the samples with a site on a solid support such that the molecules are detected in aggregate during a detection step, wherein the site comprises at least two different types of molecules; (d) obtaining a biosignature for molecules associated with the site by i) detecting a signal corresponding to the aggregate of the molecules at the site; ii) estimating the fraction of different types of molecules at the site or the amount of signal corresponding to different types of molecules at the site; iii) calculating the amount of signal corresponding to different types of molecules at the site using the fraction estimate, or calculating the fraction of different types of molecules at the site using the signal estimate; and iv) iteratively updating the fraction estimate and signal estimate until the estimates converge, thereby obtaining a biosignature for molecules at the site; and (e) comparing the biosignature obtained in step (d) to a reference biosignature, thereby identifying said biosignature.

69. The method of paragraph 68, wherein the molecules are attached at the site.

70. The method of paragraph 70, wherein the molecules comprise nucleic acids.

71. The method of paragraph 70, wherein said nucleic acids comprises a marker from a pathogen.

72. The method of paragraph 71, wherein the pathogen comprises a pathogen selected from the group consisting of a virus, a bacterium and a eukaryotic cell.

73. The method of paragraph 72, wherein the eukaryotic cell comprises a cancer cell.

74. The method of paragraph 68, wherein the sample comprises an abnormal cell type.

75. The method of paragraph 68, wherein the sample comprises a mixture of eukaryotic cell types, a mixture of microorganisms or a mixture of both eukaryotic cell types and microorganisms.

76. The method of paragraph 68, wherein the subject is not living material.

77. The method of paragraph 68, wherein the sample comprises human flora.

78. The method of paragraph 77, wherein the human flora are selected from the group consisting of skin flora, nasal flora, gut flora, vaginal flora, and oral cavity flora.

79. The method of paragraph 68, wherein the sample is obtained from a cancer patient.

80. A solid support comprising a population of nucleic acids associated with a site on said solid support such that nucleic acids of said population of nucleic acids are detected in aggregate, said population of nucleic acids comprising a first subpopulation and a second subpopulation, wherein nucleic acids of the first subpopulation comprise an identical target region and nucleic acids of the second subpopulation comprise an identical region that is a variant of the target region.

81. The solid support of paragraph 80, wherein said population of nucleic acids is associated with said site.

82. The solid support of paragraph 81, wherein about 1,000 to about 10,000 nucleic acids are associated with said site.

83. The solid support of paragraph 81, wherein about 2,000 to about 8,000 nucleic acids are associated with said site.

84. The solid support of paragraph 81, wherein about 3,000 to about 6,000 nucleic acids are associated with said site.

85. The solid support of paragraph 80, wherein a nucleotide sequence difference between the target region in first subpopulation nucleic acids and the variant of the target region in second subpopulation nucleic acids comprises at least one difference selected from the group consisting of a mutation, a polymorphism, an insertion, a deletion, a substitution, a simple tandem repeat polymorphism, and a single nucleotide polymorphism (SNP).

86. The solid support of paragraph 80, wherein said population of nucleic acids comprises alleles of a genetic locus from a polyploid organism.

87. The solid support of paragraph 80, wherein said population of nucleic acids comprises alternative splicing forms of a nucleic acid.

88. The solid support of paragraph 80, wherein said population of nucleic acids comprises alleles of a genetic locus from a diploid organism.

89. A mixture of beads comprising a plurality of beads, each bead of said plurality of beads comprising a first subpopulation and a second subpopulation of nucleic acids, wherein said first subpopulation and said second subpopulation of nucleic acids are associated with the bead such that they are detected in aggregate, wherein said nucleic acids of the first subpopulation each comprise an identical target region and said nucleic acids of the second subpopulation each comprise an identical region that is a variant of the target region.

90. The mixture of beads of paragraph 89, wherein said nucleic acids are attached to each bead of said plurality of beads.

91. The mixture of beads of paragraph 89, wherein said plurality of beads is distributed on a substrate.

92. The mixture of beads of paragraph 89 distributed on a substrate.

93. The mixture of beads of paragraph 92, wherein said distribution on the substrate is a random distribution.

94. The mixture of beads of paragraph 92, wherein said substrate comprises wells and said beads are distributed in said wells.

95. The mixture of beads of paragraph 94, wherein wells of the substrate further comprise beads having an enzyme attached thereto.

96. The mixture of beads of paragraph 95, wherein said enzyme comprises sulfurylase.

97. The mixture of beads of paragraph 95, wherein said enzyme comprises luciferase.

98. The mixture of beads of paragraph 95, wherein wells of the substrate further comprise beads having neither a nucleic acid nor enzyme attached thereto.

99. A bead comprising a first subpopulation of capture nucleic acids having a competitor molecule hybridized thereto and a second subpopulation of capture nucleic acids comprising a region that permits hybridization of a complementary molecule.

100. A bead comprising capture nucleic acids hybridized with an amplified nucleic acid comprising a degenerate tag, said degenerate tag being hybridized to a capture nucleic acid, wherein said bead is present in a channel of a substrate or wherein said bead is present in a well of a multiwell substrate, said well being configured to hold a single bead having said amplified nucleic acid hybridized thereto.

DETAILED DESCRIPTION

Aspects of the present invention relate to methods, systems and compositions for detecting multiple types of molecules associated with a solid support. Some of the methods described herein relate to detecting molecules associated with a site on a solid support, where the site comprises at least two different types of molecules. In some embodiments, the molecules are associated with a site on a solid support such that the molecules are detected in aggregate during detection. Biomolecules, such as proteins and nucleic acids, can be detected by the methods described herein. Some embodiments of these methods can be employed to detect sequences of nucleic acids associated with a site on the solid support. In some embodiments, the nucleic acids are attached at a site on the solid support. Although the detection and evaluation of molecules in aggregate is exemplified herein for embodiments in which the molecules are associated with a solid support, it will be understood that the methods and compositions can also be used for embodiments wherein the aggregation of molecules is not bound to a solid support, for example, being in solution phase.

In some embodiments of the above-described methods, detecting the molecules in aggregate involves detecting a signal corresponding to the aggregate of molecules at a site on a solid support. The aggregate signal can then be deconvoluted using processes described herein, which can be implemented using one or more data processors, such as one or more computers. In some embodiments, one step in deconvoluting the aggregate signal involves estimating the fraction of different types of molecules at the site. Alternatively or additionally, the step can involve estimating the amount of signal corresponding to different types of molecules at the site. In some embodiments, the variation associated with one or both estimates is determined. In some embodiments, the amount of signal corresponding to different types of molecules at the site is calculated based on, or otherwise using, the variation associated with the fraction estimate, thereby obtaining a signal estimate. Alternatively or additionally, the fraction of different types of molecules at the site is calculated based on, or otherwise using, the variation associated with the signal estimate, thereby obtaining a fraction estimate. In further embodiments, the fraction and signal estimates are iteratively updated until the estimates converge. At or around convergence, the estimates represent a solution set that can be used to determine the types of different molecules associated with the site, thereby detecting molecules associated with the site.

It will be appreciated that, in preferred embodiments, a first signal and/or first fraction estimate is obtained. A first signal estimate can be used to estimate the fraction, which can be either a first or subsequent fraction estimate depending on whether the fraction has been previously estimated. Similarly, a first fraction estimate can be used to estimate the signal, which can be either a first or subsequent signal estimate depending on whether the signal has been previously estimated. In preferred embodiments, the fraction and signal estimates are iteratively updated by applying one or more algorithms to determine the convergence of the estimates.

Some of the systems described herein relate to a molecule detecting system comprising a solid support comprising molecules associated with a site on the support such that the molecule are detected in aggregate, where the molecules comprise at least two different types of molecules; and a detector configured to detect the molecules associated with the site.

Some embodiments of the above-described molecule detection systems can further include a first data processing module configured to estimate the fraction of different types of molecules at the site. Alternatively or additionally, the first data processing module, or another data processing module, can be configured to estimate the amount of signal corresponding to different types of molecules at the site. In some embodiments, the first data processing module is also configured to determine the variation associated with one or both of the estimates. In other embodiments, a separate data processing module is configured to determine the variation associated with one or both of the estimates. In some embodiments, the systems can further include a second data processing module configured to calculate the amount of signal corresponding to different types of molecules at the site. In some embodiments, the amount of signal corresponding to different types of molecules at the site is calculated based on, or otherwise using, the variation associated with the fraction estimate. Additionally or alternatively, a second data processing module can be configured to calculate the fraction of different types of molecules at the site. In some embodiments, the fraction of different types of molecules at the site is calculated based on, or otherwise using, the variation associated with the signal estimate. In preferred embodiments of such systems, the systems can further include a third data processing module configured to iteratively update the fraction estimate and signal estimate.

It will be appreciated that in some embodiments described herein, a plurality of data processing functions can be included together in one or a few data processing modules. In other embodiments, data processing functions can be included separately in separate data processing modules. It will also be appreciated that a first data processing module need not be separate from a second data processing module. In some embodiments, a first data processing module, a second data processing module, as well as third and subsequent data processing modules, are part of the same data processing module.

Other methods described herein relate to identifying a target region of a nucleic acid. In such embodiments, two subpopulations of nucleic acids are associated with a site on a solid support. Nucleic acids of the first subpopulation include a first target region that is the same for such nucleic acids. Nucleic acids of the second subpopulation include a target region that is the same for such nucleic acids but which is a variant of the first target region. In some embodiments, nucleic acid sequencing is performed on the nucleic acids to generate a signal corresponding to one or more nucleotides of the target region of first subpopulation nucleic acids and one or more nucleotides of the variant of the target region of second subpopulation nucleic acids. This signal can be deconvoluted as described above, and further herein, to obtain sequence data for the target region and the variant of the target region. Sequencing can be performed using methods known in the art, including but not limited to, a sequencing by hybridization process, a sequencing by ligation process, a sequencing by exonucleolysis (for example, an exonucleolytic-nanopore process), or a sequencing-by-synthesis process (for example, a pyrosequencing process).

In some embodiments of the above-described methods for identifying a target region of a nucleic acid, signal and/or fraction estimates for the first and second subpopulations of nucleic acids can be determined. In some embodiments, the amount of signal corresponding to first subpopulation nucleic acids and second subpopulation nucleic acids associated with the site is calculated based on, or otherwise using, the fraction estimate. Alternatively or additionally, the fraction of first subpopulation nucleic acids and second subpopulation nucleic acids associated with the site is calculated based on, or otherwise using, the signal estimate. In preferred embodiments, the fraction estimate and signal estimates are iteratively updated until the estimates converge. In such a way, the target region of the nucleic acids of the subpopulations can be identified.

Additional methods described herein relate to identifying a biosignature. In some embodiments of such methods, samples from a plurality of subjects are investigated. Such samples comprise molecules, such as nucleic acids and proteins. In a preferred embodiment, at least some of the molecules from the samples are tagged to permit identification of the subject from which each sample originated. However, addition of an extrinsic tag is optional. In some embodiments tags that are intrinsic to the molecules, such as distinguishable nucleotide sequences in the case of nucleic acid molecules, can be used. In some embodiments, the molecules are then associated with a site on a solid support such that the molecules are detected in aggregate during a detection step. As discussed in connection with other methods described herein, the site comprises at least two different types of molecules.

In some embodiments, a biosignature is obtained for a population or subpopulation of molecules associated with the site. In certain embodiments, obtaining a biosignature is performed by detecting a signal corresponding to the aggregate of the molecules at the site and then deconvoluting the aggregate signal as described in connection with the methods set out above and elsewhere herein. In a preferred embodiment, the biosignature that is obtained is compared to a reference biosignature, thereby permitting identification of the biosignature.

Some of the compositions described herein relate to a solid support comprising a population of nucleic acids associated with a site on the solid support such that nucleic acids of the population of nucleic acids are detected in aggregate. In some embodiments, the population of nucleic acids comprises a first subpopulation and a second subpopulation, wherein nucleic acids of the first subpopulation comprise an identical target region and nucleic acids of the second subpopulation comprise an identical region that is a variant of the target region.

Other compositions described herein relate to mixtures of beads comprising a plurality of beads. In some embodiments, each bead of the plurality of beads comprises a first subpopulation and a second subpopulation of nucleic acids, wherein the first subpopulation and the second subpopulation of nucleic acids are associated with the bead such that they are detected in aggregate. In some embodiments, the nucleic acids of the first subpopulation each comprise an identical target region and the nucleic acids of the second subpopulation each comprise an identical region that is a variant of the target region. The variant can be one or more nucleotides of a sequence region. In particular embodiments the variant is a single nucleotide such as the type present in single nucleotide polymorphism (SNP).

Other compositions described herein relate to beads comprising a first subpopulation of capture nucleic acids having a competitor molecule hybridized thereto and a second subpopulation of capture nucleic acids comprising a region that permits hybridization of a complementary molecule.

Still other compositions described herein relate to beads comprising capture nucleic acids hybridized with an amplified nucleic acid comprising a degenerate tag. In some embodiments, a degenerate tag is hybridized to a capture nucleic acid, wherein the bead is present in a channel of a substrate. In some embodiments, the bead is present in a well of a multiwell substrate. In some embodiments, the well is configured to hold a single bead having the amplified nucleic acid hybridized thereto.

DEFINITIONS

As used herein, "oligonucleotide," "polynucleotide," "nucleic acid" and/or grammatical equivalents thereof can refer to at least two nucleotide monomers linked together. A nucleic acid can generally contain phosphodiester bonds, however, in some embodiments, nucleic acid analogs may have other types of backbones, comprising, for example, phosphoramide (Beaucage, et al., Tetrahedron, 49:1925 (1993); Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986), incorporated by reference in their entireties), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989), incorporated by reference in its entirety), O-methylphosphoroamidite linkages (see Eckstein, Oligonucleotides and Analogues: A Practical Approach, Oxford University Press, incorporated by reference in its entirety), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), incorporated by reference in their entireties). In some embodiments, oligonucleotide, polynucleotide and/or nucleic acid refer to at least five nucleotides linked together, at least 10 nucleotides linked together, at least 15 nucleotides linked together, at least 20 nucleotides linked together or at least 25 nucleotides linked together.

Other analog nucleic acids include those with positive backbones (Denpcy, et al., Proc. Natl. Acad. Sci. USA, 92:6097 (1995), incorporated by reference in its entirety); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996), incorporated by reference in their entireties) and non-ribose (U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Coo, incorporated by reference in their entireties). Nucleic acids may also contain one or more carbocyclic sugars (see Jenkins, et al., Chem. Soc. Rev., (1995) pp. 169 176).

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole (Loakes et al., Nucleic Acid Res. 22:4039 (1994); Van Aerschot et al., Nucleic Acid Res. 23:4363 (1995); Nichols et al., Nature 369:492 (1994); Berstrom et al., Nucleic Acid Res. 25:1935 (1997); Loakes et al., Nucleic Acid Res. 23:2361 (1995); Loakes et al., J. Mol. Biol. 270:426 (1997); and Fotin et al., Nucleic Acid Res. 26:1515 (1998), incorporated by reference in their entireties). Promiscuous bases that can base-pair with at least three, four or more types of bases can also be used.

As used herein, "nucleotide" and/or grammatical equivalents thereof can refer to a nucleotide and/or nucleotide analog. In some embodiments, nucleotides can become incorporated into a polynucleotide. In some embodiments, nucleotides may be substrates for an enzyme that can extend a polynucleotide strand. Nucleotides may or may not become incorporated into a nascent polynucleotide in template-based polynucleotide synthesis. Nucleotides may or may not contain labels and/or terminators. In some embodiments, terminators include reversibly terminating moieties. Incorporation of a nucleotide comprising a reversible terminator can inhibit extension of the polynucleotide; however, the moiety can be removed and the polynucleotide may then be extended further. Such reversible terminators are known in the art examples of which are described in U.S. Pat. No. 7,541,444; U.S. Pat. No. 7,057,026; U.S. Pat. No. 7,414,116; U.S. Pat. No. 7,427,673; U.S. Pat. No. 7,566,537; U.S. Pat. No. 7,592,435 and WO 07/135,368, each of which is incorporated herein by reference in its entirety. In some embodiments, a nucleotide may comprise both a label and a terminator. Examples of nucleotides include deoxyribonucleotides, modified deoxyribonucleotides, ribonucleotides, modified ribonucleotides, peptide nucleotides, modified peptide nucleotides, modified phosphate sugar backbone nucleotides and mixtures thereof. Nucleotide analogs which include a modified nucleobase can also be used in the methods described herein. As is known in the art, certain nucleotide analogues cannot become incorporated into a polynucleotide, for example, nucleotide analogues such as adenosine 5' phosphosulfate. In some embodiments, the bases are promiscuous bases.

As used herein, "a portion" and/or grammatical equivalents thereof can refer to any fraction of a whole amount. In some embodiments, the term portion may be applied to any substance or process that has boundaries, a particular number of items or a beginning and an end. For example, in some embodiments, the term portion can be applied to nucleic acids, target regions of nucleic acids, variants of target regions of nucleic acids, samples, populations, subpopulations, solid supports, sites, beads and process steps. In some embodiments, "at least a portion" can refer to at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of the whole amount. In some embodiments, a portion can refer to any fraction of a whole amount that is from 0.1% to 99.9%. In some embodiments, a portion can refer to any fraction of a whole amount that is from 1% to 99%. In some embodiments, a portion can refer to any fraction of a whole amount that is from 2% to 98%. In some embodiments, a portion can refer to any fraction of a whole amount that is from 5% to 95%. In some embodiments, a portion can refer to any fraction of a whole amount that is from 10% to 90%. In some embodiments, a portion can refer to any fraction of a whole amount that is from 20% to 90%. In some embodiments, a portion can refer to any fraction of a whole amount that is from 30% to 90%.

As used herein, "fraction" and/or grammatical equivalents thereof means any part of a whole composition or process, the absence of a whole composition or process or the presence of the whole composition or process. For example, in some embodiments, the term fraction can be applied to populations and/or subpopulations of molecules. In some such embodiments, where molecules are associated with a site on a solid support, fraction can be used to refer to a part of the population or subpopulation of molecules present at the site. For example, if three different types of molecules are thought to be present at a site, then the population of molecules present at the site can be divided into three fractions, each of which represents a particular type of molecule in the population or subpopulation.

As used herein, "detected in aggregate" and/or grammatical equivalents thereof can refer to the manner in which the molecules at a site on a solid support are detected. In some embodiments, "detected in aggregate" means that molecules present at a site, which are separately associated with or separately attached at the site, are detected together. In some embodiments, the molecules need not be separately associated with or separately attached at the site. In some embodiments, the entire population of molecules at the site is detected. In other embodiments, only a portion of the entire population of molecules at the site is actually detected.

In some embodiments, detection may be indirect as in pyrosequencing. For example, a detectable signal can be produced by a molecule that is in proximity of the molecule to be detected but which is not attached to the detected molecule. In other embodiments, detection can be direct as in the case of a label attached to a molecule associated with a site. For example, in some embodiments, a labeled molecule can be incorporated into a nucleic acid in sequencing by synthesis applications. In some embodiments, direct detection can occur even if the label is attached to the molecule through one or more intermediary molecules.

As used herein, the term "complementary" and/or grammatical equivalents thereof refer to the nucleotide base-pairing interaction of one nucleic acid with another nucleic acid that results in the formation of a duplex, triplex, or other higher-ordered structure. In some embodiments, the nucleic acids are similar enough in complementarity between sequences to permit hybridization under various stringency conditions. As will be appreciated by persons skilled in the art, stringent conditions are sequence-dependent and are different in different circumstances. For example, longer fragments may require higher hybridization temperatures for specific hybridization than short fragments. Because other factors, such as base composition and length of the complementary strands, presence of organic solvents, and the extent of base mismatching, may affect the stringency of hybridization, the combination of parameters can be more important than the absolute measure of any one parameter alone. In some embodiments, hybridization can be made to occur under high stringency conditions, such as high temperatures or 0.1×SCC. Examples of high stringent conditions are known in the art; see for example Sambrook et al., Molecular Cloning: A Laboratory Manual, 2d Edition, 1989, and Short Protocols in Molecular Biology, ed. Ausubel et al., both of which are hereby incorporated by reference. In general, increasing the temperature at which the hybridization is performed increases the stringency. As such, the hybridization reactions described herein can be performed at a different temperature depending on the desired stringency of hybridization. Hybridization temperatures can be as low as, or even lower than, 5° C., but are typically greater than 22° C., and more typically greater than about 30° C., and even more typically in excess of 37° C. In other embodiments, the stringency of the hybridization can further be altered by the addition or removal of components of the buffered solution. In some embodiments, hybridization is permitted under medium stringency conditions. In other embodiments, hybridization is permitted under low stringency conditions. In some embodiments, a nucleic acid sequence is perfectly complementary to a capture nucleic acid or other molecule with which it binds. In other embodiments, one or more mismatches are present between the hybridized molecules or hybridized portions of molecules.

As used herein the term "type of molecule" and/or grammatical equivalents thereof are intended to refer to any grouping of molecules that can be based on either natural or artificial criteria. For example, in some embodiments, two nucleic acids having an identical sequence but for a single nucleotide difference can be considered different types of molecules. In other embodiments, polypeptides having identical amino acid sequence but for a single amino acid difference can be considered different types of molecules. In some embodiments, difference may be based on differences in sequence length or other higher level structural arrangements including, but not limited to, secondary, tertiary and quaternary structures. In some embodiments, type of molecule can refer to the class of molecule. For example, nucleic acids and proteins are different classes of molecules, and thus, can be considered different types of molecules.

In some embodiments, a portion of a molecule can be used to characterize molecules as different types of molecules. For example, a portion of the molecule used to characterize a molecule can be a portion of the primary sequence of a polymeric molecule, such as a nucleotide or amino acid sequence, or a portion of another structural feature, such as nucleic acid or polypeptide secondary structure. In some embodiments, the portion of the molecule is a stretch or region of contiguous or noncontiguous nucleotide sequence. In some embodiments, "a target region" of a molecule, such as a nucleic acid, is a portion of the molecule, which is less than the entirety of the nucleotide sequence. In such embodiments, the target region of a nucleic acid can be characterized with respect to a region of another nucleic acid as either identical or a variant. In such embodiments, if the nucleotide sequence of the target region of a first nucleic acid is identical to a region of a second nucleic acid, then the molecules can be characterized as the same type of molecule. If the nucleotide sequence of the target region of a first nucleic acid has one or more nucleotide differences with respect to a region of a second nucleic acid, then the molecules can be characterized as different types of molecules. In such embodiments, the region of the second nucleic acid is referred to as a "variant of the target region."

As used herein, the term "estimating," "approximating" and/or grammatical equivalents thereof include, but are not limited to, estimating based on no knowledge about the particular system being analyzed or similar systems, for example, guessing or random number generation. In some embodiments, estimating can be based on some knowledge about the particular system being analyzed or similar systems. For example, principle component analysis of the system under investigation or a similar system can provide information that can be used to generate numerical estimates that may be closer to the actual numeric values of one or more parameters being investigated in connection with a particular system.

As used herein, the term "data processing module" and/or grammatical equivalents thereof refer to a module that processes data. A data processing module can be implemented in hardware, software or a combination of both. In some embodiments, multiple data processing modules can be combined. In some embodiments, the functionality of multiple data processing modules is implemented in a single data processing module. In other embodiments, data processing modules are separate. In some embodiments, data processing instructions included in one or more data processing modules can be executed by a single CPU. In other embodiments, such instructions may be implemented by multiple CPUs.

As used herein, the term "site" and/or grammatical equivalents thereof refer to a location on a solid support. In some embodiments, a site refers to a location on a solid support where molecules are associated together in close proximity. In some embodiments, the molecules are present at the site in such a fashion that signal produced in the detection of the molecules is detected as an aggregate signal. For example, the resolution of the detection system may be at a level that can only detect an aggregate signal form a site and cannot distinguish individual signals from different molecules at the site. In some embodiments, the signals corresponding to molecules of different types that are associated with a site cannot be adequately resolved from each other. In some embodiments, a site is a specific area on a large solid support, such as a site on a solid substrate, such as a flow cell. In other embodiments, a site includes the entire solid support as in the case of certain beads, such as microbeads. As such, in some embodiments "a site on a solid support" can refer to a portion of a solid support, whereas in other embodiments, a site on a solid support can refer to the entire solid support.

In some embodiments of the methods, systems and compositions described herein, the term "site" means a feature of a microarray. In some embodiments, a site has a certain number of molecules associated therewith. In other embodiments, a site has a number of molecules within a specified range associated therewith. For example, in some embodiments, a site includes about 2 to about $10^{11}$ molecules, about 2 to about $10^{10}$ molecules, about 2 to about $10^{9}$ molecules, about 2 to about $10^{8}$ molecules, about 2 to about $10^{7}$ molecules, about 2 to about $10^{6}$ molecules, about 2 to about $10^{5}$ molecules or about 2 to about $10^{4}$ molecules. In other embodiments, a site includes about 10 to about $10^{11}$ molecules, about 10 to about $10^{10}$ molecules, about 10 to about $10^{9}$ molecules, about 10 to about $10^{8}$ molecules, about 10 to about $10^{7}$ molecules, about 10 to about $10^{6}$ molecules, about 10 to about $10^{5}$ molecules or about 10 to about $10^{4}$ molecules. In still other embodiments, the site includes about 50 to about $10^{11}$ molecules, about 50 to about $10^{10}$ molecules, about 50 to about $10^{9}$ molecules, about 50 to about $10^{8}$ molecules, about 50 to about $10^{7}$ molecules, about 50 to about $10^{6}$ molecules, about 50 to about $10^{5}$ molecules or about 50 to about $10^{4}$ molecules. In yet other embodiments, a site includes about 100 to about $10^{11}$ molecules, about 100 to about $10^{10}$ molecules, about 100 to about $10^{9}$ molecules, about 100 to about $10^{8}$ molecules, about 100 to about $10^{7}$ molecules, about 100 to about $10^{6}$ molecules, about 100 to about $10^{5}$ molecules or about 100 to about $10^{4}$ molecules associated therewith.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In some embodiments, a site includes less area than the area of the entire solid support surface, such as a microarray surface, where molecules are associated. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, less than 0.00001%, less than $10^{-6}$%, less than $10^{-7}$%, less than $10^{-8}$%, less than 10%, less than $10^{-10}$% or less than $10^{-11}$% of the totality of the solid support surface, such as a microarray surface, where molecules are associated. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, less than 0.00001%, less than $10^{-6}$%, less than $10^{-7}$%, less than $10^{-8}$%, less than 10%, less than $10^{-10}$% or less than $10^{-11}$% of the totality of a demarcated area on an array substrate, whether physically or virtually demarcated, where molecules are associated.

In some embodiments, a site is a feature having its longest dimension in the micron range, which can accommodate a plurality of nucleic acids detectable and/or resolvable by current optical imaging devices such as scanners. In some embodiments, the site is a feature of about 0.1 square micron, 0.2 square microns, 0.3 square microns, 0.4 square microns, 0.5 square microns, 0.6 square microns, 0.7 square microns, 0.8 square microns, 0.9 square microns, 1.0 square microns, 1.1 square microns, 1.2 square microns, 1.3 square microns, 1.4 square microns, 1.5 square microns, 1.6 square microns, 1.7 square microns, 1.8 square microns, 1.9 square microns, 2 square microns, 3 square microns, 4 square microns, 5 square microns, 6 square microns, 7 square microns, 8 square microns, 9 square microns, 10 square microns, 11 square microns, 12 square microns, 13 square microns, 14 square microns, 15 square microns, 20 square microns, 25 square microns, 30 square microns, 35 square microns, 40 square microns, 45 square microns, to about 50 square microns, or any size in between any of the foregoing values.

In other embodiments, a site is a feature having its longest dimension in the sub-micron range that accommodates a plurality of nucleic acids detectable and/or resolvable by current imaging devices such as scanners. In some embodiments, the site is a feature size of about 1 square nanometer, 5 square nanometers, 10 square nanometers, 15 square nanometers, 20 square nanometers, 25 square nanometers, 30 square nanometers, 35 square nanometers, 40 square nanometers, 45 square nanometers, 50 square nanometers, 55 square nanometers, 60 square nanometers, 65 square nanometers, 70 square nanometers, 75 square nanometers, 80 square nanometers, 85 square nanometers, 90 square nanometers, 95 square nanometers, 100 square nanometers, 125 square nanometers, 150 square nanometers, 175 square nanometers, 200 square nanometers, 225 square nanometers, 250 square nanometers, 275 square nanometers, 300 square nanometers, 325 square nanometers, 350 square nanometers, 375 square nanometers, 400 square nanometers, 425 square nanometers, 450 square nanometers, 475 square nanometers, 500 square nanometers, 525 square nanometers, 550 square nanometers, 575 square nanometers, 600 square nanometers, 625 square nanometers, 650 square nanometers, 675 square nanometers, 700 square nanometers, 725 square nanometers, 750 square nanometers, 775 square nanometers, 800 square nanometers, 825 square nanometers, 850 square nanometers, 875 square nanometers, 900 square nanometers, 925 square nanometers, 950 square nanometers, 975 square nanometers to about 1000 square nanometers, or any size in between any of the foregoing values.

It will be understood that some embodiments contemplate a site that is a feature in the picometer range. Accordingly, in some embodiments, the site is a feature of about 1 square picometer, 5 square picometers, 10 square picometers, 15 square picometers, 20 square picometers, 25 square picometers, 30 square picometers, 35 square picometers, 40 square picometers, 45 square picometers, 50 square picometers, 55 square picometers, 60 square picometers, 65 square picometers, 70 square picometers, 75 square picometers, 80 square picometers, 85 square picometers, 90 square picometers, 95 square picometers, 100 square picometers, 125 square picometers, 150 square picometers, 175 square picometers, 200 square picometers, 225 square picometers, 250 square picometers, 275 square picometers, 300 square picometers, 325 square picometers, 350 square picometers, 375 square picometers, 400 square picometers, 425 square picometers, 450 square picometers, 475 square picometers, 500 square picometers, 525 square picometers, 550 square picometers, 575 square picometers, 600, 625 square picometers, 650 square picometers, 675 square picometers, 700 square picometers, 725 square picometers, 750 square picometers, 775 square picometers, 800 square picometers, 825 square picometers, 850 square picometers, 875 square picometers, 900 square picometers, 925 square picometers, 950 square picometers, 975 square picometers to about 1000 square picometers, or any size in between any of the foregoing values.

As used herein, "biosignature" and/or grammatical equivalents thereof comprises information that indicates the presence, absence and/or identity of a molecule or a plurality of molecules in a population of molecules or a subpopulation of molecules. In some embodiments, a biosignature comprises information that indicates whether a single type of molecule is present or absent in a population or subpopulation of molecules. In other embodiments, a biosignature comprises information that indicates whether different types of molecules are present or absent in a population or subpopulation of molecules. In other embodiments, a biosignature comprises information that indicates the identity of a single type of molecule or a portion of a single type of molecule that is present or absent in a population or subpopulation of molecules. In other embodiments, a biosignature comprises information that indicates the identities of different types of molecules or portions of different types of molecules that are present or absent in a population or subpopulation of molecules. In still other embodiments, a biosignature comprises any combination of the above-described information. In a preferred embodiment, a biosignature comprises information that indicates the presence, absence and/or identity of a plurality of different types of molecules in a population of molecules, or a subpopulation of molecules, associated with a site on a solid support.

As used herein, "reference biosignature" means a biosignature that is known to be a characteristic of a group of organisms or group of other entities comprising biomolecules. In some embodiments, a reference biosignature is a biosignature that is known to be a characteristic of a species or variety of organism.

By "capture probe," "capture nucleic acid" and/or grammatical equivalents thereof is meant a polynucleotide that is associated with a solid support and that is used to hybridize with nucleic acid having at least a portion complimentary to the capture probe.

As used herein, "solid support" and/or grammatical equivalents thereof means any solid or semi-solid substrate to which molecules can be associated. In some embodiments, a solid support is a solid substrate. In some embodiments, a solid support includes a plurality of sites. In some embodiments, a solid support can comprises a bead or other microparticle. In other embodiments, a solid support comprises a flow chamber or flow cell. In some embodiments, the solid support comprises one or more arrays or microarrays.

Nucleic Amplification

Embodiments of the methods, systems and compositions described herein can be implemented with or without amplification of the molecules associated with a site on a solid support. In preferred embodiments, the molecules are amplified using standard techniques known in the art. In some embodiments, the molecules are amplified prior to associating the molecules with the site on the solid support. In other embodiments, the molecules are amplified subsequent to associating the molecules with the site on the solid support. In still other embodiments, the molecules are amplified both prior to and subsequent to associating the molecules with the site on the solid support.

Nucleic acid amplification includes the process of amplifying or increasing the numbers of a nucleic acid molecule template and/or of a complement thereof that are present, by producing one or more copies of the template and/or or its complement. In the provided methods, amplification can be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010,251; which are incorporated by reference herein in their entireties. Briefly, in the provided methods, amplification can occur on a surface to which one or more template nucleic acid molecules are attached. This type of amplification can be referred to as solid phase amplification, which when used in reference to nucleic acids, refers to any nucleic acid amplification reaction carried out on or in association with a surface (e.g., a solid support). Typically, all or a portion of the amplified products are synthesized by extension of an immobilized primer. Solid phase amplification reactions are analogous to standard solution phase amplifications except that at least one of the amplification primers is immobilized on a surface (e.g., a solid support).

Solid-phase amplification may involve a nucleic acid amplification reaction including only one species of oligonucleotide primer immobilized to a surface. Alternatively, the surface may have a plurality of first and second different immobilized oligonucleotide primer species. Solid phase nucleic acid amplification reactions generally include at least one of two different types of nucleic acid amplification, interfacial and surface (or bridge) amplification. For instance, in interfacial amplification the solid support includes template nucleic acid molecules that are each indirectly immobilized to the solid support by hybridization to an immobilized oligonucleotide primer, the immobilized primer may be extended in the course of a polymerase-catalyzed, template-directed elongation reaction (e.g., primer extension) to generate an immobilized nucleic acid molecule that remains attached to the solid support. After the extension phase, the nucleic acids (e.g., template and its complementary product) are denatured such that the template nucleic acid molecules are released into solution and each made available for hybridization to another immobilized oligonucleotide primer. The template nucleic acid molecules may be made available in 1, 2, 3, 4, 5 or more rounds of primer extension or may be washed out of the reaction after 1, 2, 3, 4, 5 or more rounds of primer extension.

In surface (or bridge) amplification, immobilized nucleic acid molecules each hybridize to an immobilized oligonucleotide primer. The immobilized nucleic acid molecule provides the template for a polymerase-catalyzed, template-directed elongation reaction (e.g., primer extension) extending from the immobilized oligonucleotide primer. The resulting double-stranded products "bridge" the two primers and both strands are covalently attached to the support. In the next cycle, following denaturation that yields a pair of single strands (the immobilized template and the extended-primer product) immobilized to the solid support, both immobilized strands can serve as templates for new primer extension.

Amplification methods can be used to produce clusters of immobilized nucleic acid molecules. For example, the methods can produce arrays of nucleic acid clusters, analogous to those described in U.S. Pat. No. 7,115,400; U.S. Publication No. 2005/0100900; WO 00/18957; and WO 98/44151, which are incorporated by reference herein in their entireties. A cluster is a plurality of nucleic acid molecules attached to a site on a surface. A cluster can include a plurality of copies of a single nucleic acid sequence or a plurality of copies of a plurality of nucleic acid sequences. The nucleic acid molecules making up the clusters may be in a single or double stranded form.

The clusters can have different shapes, sizes and densities depending on the conditions used. For example, clusters can have a shape that is substantially round, multi-sided, donut-shaped or ring-shaped. The diameter or maximum cross section of a cluster can be the same or similar as those set forth above for sites in general. The density of clusters or other sites can be in the range of at least about $0.1/mm^2$, at least about $1/mm^2$, at least about $10/mm^2$, at least about $100/mm^2$, at least about $1,000/mm^2$, at least about $10,000/mm^2$ to at least about $100,000/mm^2$. Optionally, the clusters have a density of, for example, $100,000/mm^2$ to $1,000,000/mm^2$ or $1,000,000/mm^2$ to $10,000,000/mm^2$.

Detection of Multiple Molecules in Aggregate

Disclosed herein are methods that can be used for detecting in aggregate multiple molecules that are associated with a site on a solid support, where the site comprises at least two different types of molecules. In some embodiments, detecting multiple molecules in aggregate can include the steps of detecting a signal corresponding to the aggregate of molecules at the site; estimating the fraction of different types of molecules at the site, or estimating the amount of signal corresponding to different types of molecules at the site; calculating the amount of signal corresponding to different types of molecules at the site using the fraction estimate, thereby obtaining a signal estimate or calculating the fraction of different types of molecules at the site using the signal estimate, thereby obtaining a fraction estimate; and iteratively updating the fraction estimate and signal estimate until the estimates converge, thereby detecting molecules attached at the site.

In some embodiments, a mixture of molecules is provided to the solid support or to a site on the solid support. In some embodiments, the mixture of molecules can include one type of molecule, for example, molecules having an identical target region. In other embodiments, the mixture of molecules can include a plurality of molecule types, for example, some molecules each having an identical target region and other molecules having one or more variants of a target region.

In some embodiments, a mixture of molecules is associated with a site on the solid support. Molecules can be associated with a solid support either directly or indirectly. In some embodiments, molecules are coupled to a solid support without attaching them to the solid support, such as by dissolving or suspending the molecules in a droplet on the surface of a solid support. In other embodiments, molecules can be associated with a solid support by coupling the molecules to a first solid support, such as a bead, which itself is associated with a second solid support, such as an array surface, a well on an array or a flow chamber.

In some embodiments, the molecules are attached at a site on a solid support. The attachment can be direct bonding or adhesion to a surface of the solid support or indirect attachment. Examples of indirect attachment include, but are not limited to, attachment of the molecules to the solid support via a linker molecule or a capture nucleic acid. In some embodiments, indirect attachment can include attaching molecules to a first solid support, such as a bead, which itself is attached to a second solid support, such as an array surface, a well on an array or a flow chamber.

In some embodiments, the multiple types of molecules at the site that are detected in aggregate have a linear relationship, that is, the presence of one type of molecule at the site does not influence other type(s) of molecule at the site. For example, if there are two different types of nucleic acids at the site, allele 1 and allele 2, the value of signal (fraction 1*allele1+fraction 2*allele 2) is expected to be substantially similar to the value of fraction 1*signal (allele 1)+fraction 2*signal (allele 2). As another example, if the three different types of nucleic acids at the site are allele 1, allele 2 and allele 3, the value of signal (fraction 1*allele1+fraction 2*allele 2+fraction 3*allele 3) is expected to be substantially similar to the value of fraction 1*signal (allele 1)+fraction 2*signal (allele 2)+fraction 3*signal (allele 3). In some embodiments, a principal component analysis (PCA) can be used to determine the linearity between the different types of molecules at the site. PCA is known in the art and has been described by Jolliffe, I. T. Principal Component Analysis Series: Springer Series in Statistics, $2^{nd}$ ed., Springer, N.Y. 2002, the disclosure of which is incorporated herein by reference in its entirety.

The methods described herein can detect more than two types of molecules at a site in aggregate. In some embodiments, the site comprises at least three, four or five different types of molecules. In other embodiments, the site comprises at least six, seven or eight different types of molecules. In still other embodiments, the site comprises at least nine, ten, eleven, twelve, thirteen, fourteen, fifteen, or more different types of molecules. In some embodiments, two different types of molecules are detected in aggregate. In other embodiments, three, four or five different types of molecules are detected in aggregate. In still other embodiments, six, seven or eight different types of molecules are detected in aggregate. In yet other embodiments, nine, ten, eleven, twelve, thirteen, fourteen, fifteen, or more different types of molecules are detected in aggregate. Additionally or alternatively, there can be a cap to the number of different types of molecules at a site including, for example, at most about fifteen, fourteen, thirteen, twelve, eleven, ten, nine, eight, seven, six, five, four, three, or two. The number of different types of molecules at a site or detected in an aggregate can be within a range defined by the values exemplified above or can be outside of these ranges depending upon the embodiment employed.

Different number of molecules can be associated with a site on a solid support. In some embodiments, about 2 to about 100,000 molecules are associated with the site. In other embodiments, about 10 to about 90,000, or about 100 to about 80,000, or about 500 to 70,000, or about 600 to about 60,000, or about 600 to about 50,000, or about 700 to about 40,000, or about 800 to about 30,000, or about 900 to about 20,000, or about 1,000 to about 10,000, or about 2,000 to about 8,000, or about 3,000 to about 6,000, or about 4,000 to about 5,000 molecules are associated with the site.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In some embodiments of the molecule detection methods described herein, a site includes a population of molecules ranging from about 2 to about $10^{11}$ molecules, about 2 to about $10^{10}$ molecules, about 2 to about $10^9$ molecules, about 2 to about $10^8$ molecules, about 2 to about $10^7$ molecules, about 2 to about $10^6$ molecules, about 2 to about $10^5$ molecules or about 2 to about $10^4$ molecules. In other embodiments, a site includes about 10 to about $10^{11}$ molecules, about 10 to about $10^{10}$ molecules, about 10 to about $10^9$ molecules, about 10 to about $10^8$ molecules, about 10 to about $10^7$ molecules, about 10 to about $10^6$ molecules, about 10 to about $10^5$ molecules or about 10 to about $10^4$ molecules. In still other embodiments, the site includes about 50 to about $10^{11}$ molecules, about 50 to about $10^{10}$ molecules, about 50 to about $10^9$ molecules, about 50 to about $10^8$ molecules, about 50 to about $10^7$ molecules, about 50 to about $10^6$ molecules, about 50 to about $10^5$ molecules or about 50 to about $10^4$ molecules. In yet other embodiments, a site includes about 100 to about $10^{11}$ molecules, about 100 to about $10^{10}$ molecules, about 100 to about $10^9$ molecules, about 100 to about $10^8$ molecules, about 100 to about $10^7$ molecules, about 100 to about $10^6$ molecules, about 100 to about $10^5$ molecules or about 100 to about $10^4$ molecules. In a preferred embodiment, the entire population of molecules present at a site is detected in aggregate. In another preferred embodiment, one or more portions of the population of molecules is detected in aggregate.

In some embodiments, detection can occur by detecting a signal produced by the molecules, such as a signal produced by a label attached directly to the molecule. In a preferred embodiment, the label is a fluorescent label. In other embodiments, detection can occur by detecting a signal produced by a one or more labeled molecules hybridized to, or otherwise attached to, the molecules. In some embodiments, detection can occur by detecting a signal produced in close proximity to the molecules. For example, the signal may be a diffusible signal that is generated by the production of a particular detectable compound or by the production of a particular enzymatic substrate that is converted into a detectable compound. In some embodiments, the compound may be a diffusible compound.

In some embodiments of the methods described herein, a first estimate is made. In some embodiments, the first estimate is an estimate of the fraction of different types of molecules at the site. In other embodiments, the first estimate is an estimate of the amount of signal corresponding to different types of molecules at the site. In a preferred embodiment, the estimate of the fraction of different types of molecules at the site is a matrix of values, wherein each value corresponds to the estimated fraction of each type of molecule predicted or thought to be in the mixture of molecules associated with the site. In another preferred embodiment, the estimate of the amount of signal corresponding to different types of molecules at the site is a matrix of values, wherein each value corresponds to the estimated amount of combined signal generated by each type of molecule predicted or thought to be in the mixture of molecules associated with the site.

Once the first estimate is obtained, the variation associated with that estimate can be determined. Methods of determining the variation associated with an estimate are further exemplified below. The variation associated with the first estimate can then be used to calculate an estimate for either the fraction of different types of molecules at the site or the signal corresponding to different types of molecules at the site, whichever of these values was not approximated by the first estimate. In some embodiments, this calculated estimate is referred to as a second estimate. In a preferred embodiment, the second estimate is calculated using the least squares method.

In a preferred embodiment, the first and second estimates are refined by iteratively updating the estimates. For example, the second estimate is used to refine the first estimate. Subsequently, the refined first estimate is used to generate a refined second estimate. This refined second estimate can then be used to re-refine the first estimate, which can then be used to re-refine the second estimate. This iterative process can continue until the estimates converge on a solution set.

In some embodiments, the initial estimation is performed by guessing. For example, the estimating step can be performed by guessing the fraction of different types of molecules at the site or guessing the amount of signal corresponding to different types of molecules at the site. For example, a guess can be random or can be based on the expected distribution of different types of molecules expected for a particular sample, for example based on statistical methods. In either case, the variation associated with the guess can then be determined. In some embodiments, the initial estimation is performed through random number generation. For example, the estimating step can be performed by picking a random number for the fraction of different types of molecules at the site or picking a random number for the amount of signal corresponding to different types of molecules at the site. In some other embodiments, the initial estimation is performed based on some knowledge about the particular system being analyzed or similar systems. In some embodiments, mathematical methods known in the art, such as a principle component analysis (PCA), can be used to improve the initial fraction estimate or the initial signal estimate.

Various searching methods known in the art can be used in the estimating step and updating step in the methods described herein. Non-limiting examples of searching methods include searching with iterated maps, tree-based searching, and stochastic searching methods. In some embodiments, searching methods based on iterating a mathematical mapping can be used in iteratively updating the fraction estimate and signal estimate until the estimates converge. For example, in such embodiments, the updating step can include performing a numerical optimization algorithm. In some embodiments, an iterative map search with Fienup update rules can be used in the updating step until the fraction and signal estimates converge.

In some embodiments, the iteration number is from about 5 to about 200,000 iterations. In other embodiments, the iteration number is from about 100 to about 100,000 iterations. In preferred embodiments, the number of iterations to reach convergence ranges from approximately 100 to 500 iterations. In some embodiments, more than 500 iterations may be required; however as demonstrated in Example 1, convergence can be reached in less than 500 iterations. It will be appreciated that the iteration number typically increases with an increase number in types of molecules to be detected.

In some embodiments molecules or a mixture of molecules are associated with a bead or particle. In some such embodiments, the bead can be a microbead, nanobead or picobead. In some embodiments, the beads or particles can have regular or irregular shapes. Furthermore, beads having a range of sizes and/or surface textures can be used. In some embodiments, the beads range in size from 5 to 500 microns in diameter. In other embodiments, the beads range from 5 to 5000 nanometers in diameter. In still other embodiments, the beads range from 5 to 5000 picometers in diameter. In some embodiments, the beads are solid. In other embodiments, the beads can be porous or hollow. In such embodiments, the molecules can be associated with the bead by "trapping" the molecules within the bead. In a preferred embodiment, molecules are associated with the surface of a solid bead.

In some embodiments, the solid support includes a flow chamber. In other embodiments, the solid support includes a flow-cell. In a preferred embodiment, molecules are associated with a bead which itself is associated with a surface of a flow-cell or flow-chamber. In some embodiments, the solid support includes a multiwell plate. In some such embodiments, the molecules can be provided directly in the wells. In other such embodiments, the molecules can be associated with beads, which are provided to the wells.

In some preferred embodiments, sequence data can be obtained for two or more types of molecules. In some embodiments, sequence data can be obtained for two, three, four, five, six, seven, eight, nine, ten, eleven, twelve, thirteen, fourteen, fifteen, sixteen, seventeen, eighteen, nineteen, twenty, or more types of molecules. In some such embodiments, the nucleotide sequence of a target region of a first type of molecule is compared to the nucleotide sequence of a variant of the target region that is present in a second type of molecule.

In some embodiments, where nucleic acids are used, sequence data is obtained by a nucleic acid sequencing process, such as sequencing-by-synthesis. In some such embodiments, the nucleotide sequence of a target region of a first type of molecule is compared to the nucleotide sequence of a variant of the target region that is present in a second type of molecule.

In some embodiments, the nucleic acids comprise a first subpopulation of nucleic acids and a second subpopulation of nucleic acids, the nucleic acids of the first subpopulation each have an identical target region and the nucleic acids of the second subpopulation each have an identical region that is a variant of the target region. In some embodiments, the nucleotide sequence of the target region of the nucleic acids of the first subpopulation has at least 1, at least 2, at least 3, at least 4, at least 5, at least 6, at least 7, at least 8, at least 9, at least 10, at least 15, at least 20, at least 25, at least 50, at least 75 or at least 100 nucleotide(s) that is/are different as compared to the nucleotide sequence of the variant of the target region. Alternatively or additionally, the nucleotide sequence of the target region of the nucleic acids of the first subpopulation has at most 1, at most 2, at most 3, at most 4, at most 5, at most 6, at most 7, at most 8, at most 9, at most 10, at most 15, at most 20, at most 25, at most 50, at most 75 or at most 100 nucleotide(s) that is/are different as compared to the nucleotide sequence of the variant of the target region.

In some embodiments, a nucleotide sequence difference between the target region in the nucleic acids of the first subpopulation and the variant of the target region in the nucleic acids of the second subpopulation comprises at least one difference selected from the group consisting of a mutation, a polymorphism, an insertion, a deletion, a substitution, a simple tandem repeat polymorphism, and a single nucleotide polymorphism (SNP).

In some embodiments, the nucleic acids comprise alleles of a genetic locus from a polyploid organism. In some other embodiments, the nucleic acids comprise alternative splicing forms of a nucleic acid. In yet other embodiments, the nucleic acids comprise alleles of a genetic locus from a diploid organism.

Identification of a Target Region of a Nucleic Acid

Also disclosed herein are methods that can be used for identifying a target region of a nucleic acid. In some embodiments, the methods include the steps of (a) associating a first subpopulation of nucleic acids with a site on a solid support, wherein nucleic acids of the first subpopulation comprise an identical target region; (b) associating a second subpopulation of nucleic acids with the site on the solid support, wherein nucleic acids of the second subpopulation comprise an identical target region that is a variant of the target region of the nucleic acids of the first subpopulation; (c) detecting a signal corresponding to one or more nucleotides of the target region of first subpopulation nucleic acids and one or more nucleotides of the variant of the target region of second subpopulation nucleic acids; (d) estimating the fraction of first subpopulation nucleic acids and second subpopulation nucleic acids associated with the site or estimating the amount of signal corresponding to first subpopulation nucleic acids and second subpopulation nucleic acids associated with the site; (e) calculating the amount of signal corresponding to first subpopulation nucleic acids and second subpopulation nucleic acids associated with the site using the fraction estimate, or calculating the fraction of first subpopulation nucleic acids and second subpopulation nucleic acids associated with the site using the signal estimate; and (f) iteratively updating the fraction estimate and signal estimate until the estimates converge, thereby identifying a target region of a nucleic acid.

In some embodiments of the above-described methods, at least a first and second subpopulation of nucleic acids are associated with a site on a solid support. In a preferred embodiment, the first subpopulation nucleic acids and the second subpopulation nucleic acids are attached to the solid support at the site.

In some embodiments of the methods of identifying target regions of nucleic acids set forth herein, the target regions of the nucleic acids can be of the same or different lengths. In some embodiments, the target region can comprise at least 1 nucleotide, at least about 2 nucleotides, at least about 3 nucleotides, at least about 4 nucleotides, at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides. Alternatively or additionally, the target region can comprise at most 1 nucleotide, at most about 2 nucleotides, at most about 3 nucleotides, at most about 4 nucleotides, at most about 5 nucleotides, at most about 10 nucleotides, at most about 15 nucleotides, at most about 20 nucleotides, at most about 25 nucleotides, at most about 30 nucleotides, at most about 35 nucleotides, at most about 40 nucleotides, at most about 45 nucleotides, at most about 50 nucleotides, at most about 55 nucleotides, at most about 60 nucleotides, at most about 65 nucleotides, at most about 70 nucleotides, at most about 75 nucleotides, at most about 80 nucleotides, at most about 85 nucleotides, at most about 90 nucleotides, at most about 95 nucleotides, at most about 100 nucleotides, at most about 150 nucleotides, at most about 200 nucleotides, at most about 300 nucleotides, at most about 400 nucleotides, at most about 500 nucleotides, at most about 600 nucleotides, at most about 700 nucleotides, at most about 800 nucleotides, at most about 900 nucleotides, or at most about 1000 nucleotides.

In some embodiments of the methods of identifying target regions of nucleic acids, the estimating, determining, calculating and updating steps are performed as described above for molecule detection methods. In a preferred embodiment, estimating the fraction of first subpopulation nucleic acids and second subpopulation nucleic acids associated with the site includes performing a principal component analysis (PCA) to improve the estimation. In some embodiments of the above-described methods, the initial estimating of the amount of signal corresponding to first subpopulation nucleic acids and/or second subpopulation nucleic acids associated with the site includes performing a principal component analysis (PCA) to improve the estimation.

As discussed above, once a first estimate is obtained, it can be used to calculate an estimate for either the fraction of first and second subpopulation nucleic acids at the site or the signal corresponding to the first and second subpopulation nucleic acids at the site, whichever of these values was not approximated by the first estimate. In some embodiments, this calculated estimate is referred to as a second estimate. In a preferred embodiment, the second estimate is calculated using the least squares method.

As also discussed above, the first and second estimates are refined by iteratively updating the estimates. For example, the second estimate is used to refine the first estimate. Subsequently, the refined first estimate is used to generate a refined second estimate. This refined second estimate can then be used to re-refine the first estimate, which can then be used to re-refine the second estimate. This iterative process can continue until the estimates converge.

In some embodiments of the methods of identifying target regions of nucleic acids, a numerical optimization algorithm is performed to iteratively update the fraction estimate and signal estimate until the estimates converge. In some such embodiments, the numerical optimization algorithm is based on iterative map search. In some other embodiments, the numerical optimization algorithm is based on Fienup's iteration map.

It will be appreciated that more than two subpopulations of nucleic acids can be associated with a site. In some embodiments, three subpopulations of nucleic acids, four subpopulations of nucleic acids, five subpopulations of nucleic acids, six subpopulations of nucleic acids, seven subpopulations of nucleic acids, eight subpopulations of nucleic acids, nine subpopulations of nucleic acids, ten subpopulations of nucleic acids, twenty subpopulations of nucleic acids, thirty subpopulations of nucleic acids, forty subpopulations of nucleic acids, fifty subpopulations of nucleic acids or more than fifty subpopulations of nucleic acids can be associated with a site on a solid support.

Various numbers of nucleic acids can be associated with the site, for example, about 1 to about 100,000 nucleic acids can be associated with the site. In some embodiments, about 1,000 to about 10,000 nucleic acids are associated with the site. In some other embodiments, about 2,000 to about 8,000 nucleic acids are associated with the site. In still some other embodiments, about 3,000 to about 6,000 nucleic acids are associated with the site. In yet some other embodiments, about 4,000 to about 5,000 nucleic acids are associated with the site.

In a preferred embodiment, the initial number of nucleic acids associated with a site ranges from about 10 to about 1000 nucleic acids. In another preferred embodiment, about 10 to about 500 nucleic acids are initially associated with the site. In yet another preferred embodiment, about 10 to about 100 nucleic acids are initially associated with the site.

In some embodiments of the methods of identifying a target region of a nucleic acid described herein, a site includes about 2 to about $10^{11}$ nucleic acids, about 2 to about $10^{10}$ nucleic acids, about 2 to about $10^9$ nucleic acids, about 2 to about $10^8$ nucleic acids, about 2 to about $10^7$ nucleic acids, about 2 to about $10^6$ nucleic acids, about 2 to about $10^5$ nucleic acids or about 2 to about $10^4$ nucleic acids. In other embodiments, a site includes about 10 to about $10^{11}$ nucleic acids, about 10 to about $10^{10}$ nucleic acids, about 10 to about $10^9$ nucleic acids, about 10 to about $10^8$ nucleic acids, about 10 to about $10^7$ nucleic acids, about 10 to about $10^6$ nucleic acids, about 10 to about $10^5$ nucleic acids or about 10 to about $10^4$ nucleic acids. In still other embodiments, the site includes about 50 to about $10^{11}$ nucleic acids, about 50 to about $10^{10}$ nucleic acids, about 50 to about $10^9$ nucleic acids, about 50 to about $10^8$ nucleic acids, about 50 to about $10^7$ nucleic acids, about 50 to about $10^6$ nucleic acids, about 50 to about $10^5$ nucleic acids or about 50 to about $10^4$ nucleic acids. In yet other embodiments, a site includes about 100 to about $10^{11}$ nucleic acids, about 100 to about $10^{10}$ nucleic acids, about 100 to about $10^9$ nucleic acids, about 100 to about $10^8$ nucleic acids, about 100 to about $10^7$ nucleic acids, about 100 to about $10^6$ nucleic acids, about 100 to about $10^5$ nucleic acids or about 100 to about $10^4$ nucleic acids. In any of the above-described embodiments of the methods described herein, the nucleic acids present at a site can be detected in aggregate.

In some embodiments, the nucleotide sequence of the target region of first subpopulation nucleic acids has at least 1 nucleotide that is different as compared to the nucleotide sequence of the variant of the target region of second subpopulation nucleic acids. In some other embodiments, the nucleotide sequence of the target region of first subpopulation nucleic acids has at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95 or at least 100 nucleotides that are different as compared to the nucleotide sequence of the variant of the target region of second subpopulation nucleic acids. Alternatively or additionally, the nucleotide sequence of the target region of first subpopulation nucleic acids has at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, at most 50, at most 55, at most 60, at most 65, at most 70, at most 75, at most 80, at most 85, at most 90, at most 95 or at most 100 nucleotides that are different as compared to the nucleotide sequence of the variant of the target region of second subpopulation nucleic acids.

In some embodiments of the above-described methods, a nucleotide sequence difference between the target region in first subpopulation nucleic acids of and the variant of the target region in second subpopulation nucleic acids comprises at least one difference selected from the group consisting of a mutation, a polymorphism, an insertion, a deletion, a substitution, a simple tandem repeat polymorphism, and a single nucleotide polymorphism (SNP). In some embodiments of the above-described methods, a nucleotide sequence difference between the target region in first subpopulation nucleic acids of and the variant of the target region in second subpopulation nucleic acids comprises at least two, three, four, five, six, seven, eight, nine, ten, or more differences selected from the group consisting of a mutation, a polymorphism, an insertion, a deletion, a substitution, a simple tandem repeat polymorphism, and a single nucleotide polymorphism (SNP). Alternatively or additionally, a nucleotide sequence difference between the target region in first subpopulation nucleic acids of and the variant of the target region in second subpopulation nucleic acids comprises at most one, two, three, four, five, six, seven, eight, nine, ten, or more differences selected from the group consisting of a mutation, a polymorphism, an insertion, a deletion, a substitution, a simple tandem repeat polymorphism, and a single nucleotide polymorphism (SNP).

In some embodiments, first subpopulation nucleic acids and second subpopulation nucleic acids comprise alleles of a genetic locus from a polyploid organism. In some other embodiments, first subpopulation nucleic acids and second subpopulation nucleic acids comprise alternative splicing forms of a nucleic acid. In still some other embodiments, first subpopulation nucleic acids and second subpopulation nucleic acids comprise alleles of a genetic locus from a diploid organism.

In some embodiments, sequence data is obtained for one subpopulation of nucleic acids or both the first and second subpopulations of nucleic acid. In some such embodiments, sequence data is obtained by a sequencing-by-synthesis process, for example a pyrosequencing process. In other embodiments, the sequence data is obtained from a sequencing by ligation process. In still other embodiments, the sequence data is obtained from other sequencing processes known in the art. Various methods of sequencing nucleic acids are described further below.

Sequencing Methods

Embodiments of the methods and compositions disclosed herein relate to nucleic acid (polynucleotide) sequencing. In some methods and compositions described herein, the nucleotide sequence of a portion of a target nucleic acid or fragment thereof can be determined using a variety of methods and devices. Examples of sequencing methods include electrophoretic, sequencing by synthesis, sequencing by ligation, sequencing by hybridization, single-molecule sequencing, and real time sequencing methods. In some embodiments, the process to determine the nucleotide sequence of a target nucleic acid or fragment thereof can be an automated process. In some embodiments, capture probes can function as primers permitting the priming of a nucleotide synthesis reaction using a polynucleotide from the nucleic acid sample as a template. In this way, information regarding the sequence of the polynucleotides supplied to the array can be obtained. In some embodiments, polynucleotides hybridized to capture probes on the array can serve as sequencing templates if primers that hybridize to the polynucleotides bound to the capture probes and sequencing reagents are further supplied to the array. Methods of sequencing using arrays have been described previously in the art.

Electrophoretic sequencing methods include Sanger sequencing protocols and conventional electrophoretic techniques (Sanger, F., Nicklen, S, and Coulson, A. R. (1977) DNA sequencing with chain-terminating inhibitors. Proc. Natl. Acad. Sci. USA. 74(12), 5463-7; Swerdlow, H., Wu, S. L., Harke, H. & Dovichi, N. J. Capillary gel electrophoresis for DNA sequencing. Laser-induced fluorescence detection with the sheath flow cuvette. J. Chromatogr. 516, 61-67 (1990); Hunkapiller, T., Kaiser, R. J., Koop, B. F. & Hood, L. Large-scale and automated DNA sequence determination. Science 254, 59-67 (1991)). In such embodiments, electrophoresis can be carried out on a microfabricated device (Paegel, B. M., Blazej, R. G. & Mathies, R. A. Microfluidic devices for DNA sequencing: sample preparation and electrophoretic analysis. Curr. Opin. Biotechnol. 14, 42-50 (2003); Hong, J. W. & Quake, S. R. Integrated nanoliter systems. Nat. Biotechnol. 21, 1179-1183 (2003), the disclosures of which are incorporated herein by reference in their entireties).

In some embodiments described herein, nucleic acid sequencing is performed. Such sequencing can include, but is not limited to, sequencing-by-synthesis (SBS). In SBS, fluorescently labeled modified nucleotides are used to determine the sequence of nucleotides for nucleic acids present on the surface of a support structure such as a flowcell. Exemplary SBS systems and methods which can be utilized with the apparatus and methods set forth herein are described in US Patent Application Publication No. 2007/0166705, US Patent Application Publication No. 2006/0188901, U.S. Pat. No. 7,057,026 US Patent Application Publication No. 2006/0240439, US Patent Application Publication No. 2006/0281109, PCT Publication No. WO 05/065814, US Patent Application Publication No. 2005/0100900, PCT Publication No. WO 06/064199 and PCT Publication No. WO 07/010,251, each of which is incorporated herein by reference in its entirety.

With respect to other uses of the methods and compositions described herein, arrayed nucleic acids are treated by several repeated cycles of an overall sequencing process. In some embodiments, the attached nucleic acids are prepared such that they include an oligonucleotide primer (capture probe) hybridized to an unknown target sequence or hybridized to another template nucleic acid or polynucleotide whether the sequence identity is known or unknown. To initiate the first SBS sequencing cycle, one or more differently labeled nucleotides and a DNA polymerase can be introduced to the array. Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Following nucleotide addition, signals produced at the features on the surface can be detected to determine the identity of the incorporated nucleotide (based on the labels on the nucleotides). Reagents can then be added to remove the blocked 3' terminus (if appropriate) and to remove labels from each incorporated base. Reagents, enzymes and other substances can be removed between steps by washing. Such cycles are then repeated and the sequence of each cluster is read over the multiple chemistry cycles.

Preferred embodiments include sequencing by synthesis (SBS) techniques. SBS techniques generally involve the enzymatic extension of a nascent nucleic acid strand through the iterative addition of nucleotides against a template strand. Each nucleotide addition queries one or a few bases of the template strand. In one exemplary type of SBS, cycle sequencing is accomplished by stepwise addition of reversible terminator nucleotides containing, for example, a cleavable or photobleachable dye label. This approach is being commercialized by Solexa (now Illumina), and is also described in WO 91/06678, which is incorporated herein by reference in its entirety. The availability of fluorescently-labeled terminators in which both the termination can be reversed and the fluorescent label cleaved is important to facilitating efficient cyclic reversible termination (CRT) sequencing. Polymerases can also be co-engineered to efficiently incorporate and extend from these modified nucleotides. In particular embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, both disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. No. 7,427,673, and U.S. Pat. No. 7,057,026, the disclosures of which are incorporated herein by reference in their entireties.

In certain preferred embodiments, sequencing is performed by employing one or more versions of sequencing-by-synthesis (SBS). SBS is a process in which one or more nucleotides or oligonucleotides are sequentially added to a extending polynucleotide chain in the 5' to 3' direction to form an extended polynucleotide complementary to the template nucleic acid to be sequenced. The identity of the base present in one or more of the added nucleotide(s) can be determined in a detection or imaging step, preferably after each nucleotide incorporation. In various embodiments involving SBS, fluorescently labeled nucleotides are used in the sequencing reaction. The four different bases are each labeled with a unique fluorescent label to permit identification of the incorporated nucleotide as successive nucleotides are added. The labeled nucleoside triphosphates also can have a removable 3' blocking group to prevent further incorporation. The label of the incorporated base can be determined and the blocking group removed to permit further extension.

The labels may be the same for each type of nucleotide, or each nucleotide type may carry a different label. This facilitates the identification of incorporation of a particular nucleotide. Thus, for example modified adenine, guanine, cytosine and thymine would all have attached a different fluorophore to allow them to be discriminated from one another readily. When sequencing on arrays, a mixture of labeled and unlabelled nucleotides may be used. Detectable labels such as fluorophores can be linked to nucleotides via the base using a suitable linker. The linker may be acid labile, photolabile or contain a disulfide linkage. Preferred labels and linkages include those disclosed in U.S. Pat. No. 7,057,026. Other linkages, in particular phosphine-cleavable azide-containing linkers, may be employed in the invention as described in greater detail in US 2006/0160081. The contents of U.S. Pat. No. 7,057,026 and US 2006/0160081 are incorporated herein by reference.

Methods for detecting fluorescently labeled nucleotides generally use incident light (e.g. laser light) of a wavelength specific for the fluorescent label, or the use of other suitable sources of illumination, to excite the fluorophore. Fluorescent light emitted from the fluorophore may then be detected at the appropriate wavelength using a suitable detection system such as for example a Charge-Coupled-Device (CCD) camera, which can optionally be coupled to a magnifying device, a fluorescent imager or a con focal microscope. In embodiments involving sequencing carried out on an array, detection of an incorporated base may be performed by using a scanning microscope to scan the surface of the array with a laser and image fluorescent labels attached to the incorporated nucleotide(s). A sensitive 2-D detector, such as a charge-coupled detector (CCD), can be used to visualize the signals generated.

Other sequencing methods that use cyclic reactions can be used, such as those wherein each cycle can include steps of delivering one or more reagents to nucleic acids, for example, sequencing-by-synthesis and sequencing-by-ligation. Useful pyrosequencing reactions are described, for example, in US Patent Application Publication No. 2005/0191698 and U.S. Pat. No. 7,244,559, each of which is incorporated herein by reference. Sequencing-by-ligation reactions are described, for example, in Shendure et al. *Science* 309:1728-1732 (2005); U.S. Pat. No. 5,599,675; and U.S. Pat. No. 5,750,341, each of which is incorporated herein by reference in its entirety.

Several embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyrosequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. No. 6,210,891; U.S. Pat. No. 6,258,568 and U.S. Pat. No. 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Some embodiments include methods utilizing sequencing by hybridization techniques. In such embodiments, differential hybridization of oligonucleotide probes can be used to decode a target DNA sequence (Bains, W. and Smith, G. C. A novel method for nucleic acid sequence determination. Journal of Theoretical Biology 135(3), 303-7 (1988); Drmanac, S. et al., Accurate sequencing by hybridization for DNA diagnostics and individual genomics. Nature Biotechnology 16, 54-58 (1998); Fodor, S. P. A., Read, J. L., Pirrung, M. C., Stryer, L., Lu, A. T. and Solas, D. Light-directed, spatially addressable parallel chemical synthesis. Science 251(4995), 767-773 (1995); Southern, E. M. (1989) Analyzing polynucleotide sequences. WO 1989/10977), the disclosures of which are incorporated herein by reference in their entireties). The target DNA can be immobilized on a solid support and serial hybridizations can be performed with short probe oligonucleotides, for example, oligonucleotides 5 to 8 nucleotides in length. The extent to which specific probes bind to the target DNA can be used to infer the unknown sequence. Target DNA can also be hybridized to high density oligonucleotide arrays (Lipshutz, R. J. et al., (1995) Using oligonucleotide probe arrays to access genetic diversity. Biotechniques 19, 442-447, the disclosure of which is incorporated herein by reference in its entirety).

Some embodiments can utilize nanopore sequencing (Deamer and Akeson, 2000; Deamer and Branton, 2002; Li et al., 2003, the disclosure of which is incorporated herein by reference in its entirety). In such embodiments, the target nucleic acid or nucleotides exonucleolytically removed from the target nucleic acid pass through a nanopore. The nanopore can be a synthetic pore or biological membrane protein, such as α-hemolysin (Deamer, D. W. & Akeson, M. Nanopores and nucleic acids: prospects for ultrarapid sequencing. Trends Biotechnol. 18, 147-151 (2000), the disclosure of which is incorporated herein by reference in its entirety). As the target nucleic acid or nucleotides derived therefrom pass through the nanopore, each type of base can be identified by measuring fluctuations in the electrical conductance of the pore. (U.S. Pat. No. 7,001,792; Soni, G. V. & Meller, A. Progress toward ultrafast DNA sequencing using solid-state nanopores. Clin. Chem. 53, 1996-2001 (2007); Healy, K. Nanopore-based single-molecule DNA analysis. Nanomed. 2, 459-481 (2007); Cockroft, S. L., Chu, J., Amorin, M. & Ghadiri, M. R. A single-molecule nanopore device detects DNA polymerase activity with single-nucleotide resolution. J. Am. Chem. Soc. 130, 818-820 (2008); Levene, M. J. et al. Zero-mode waveguides for single-molecule analysis at high concentrations. Science 299, 682-686 (2003), the disclosures of which are incorporated herein by reference in their entireties).

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides. The illumination can be restricted to a zeptoliter-scale volume around a surface-tethered polymerase such that incorporation of fluorescently labeled nucleotides can be observed with low background (Levene, M. J. et al. Zero-mode waveguides for single-molecule analysis at high concentrations. Science 299, 682-686 (2003); Lundquist, P. M. et al. Parallel confocal detection of single molecules in real time. Opt. Lett. 33, 1026-1028 (2008); Korlach, J. et al. Selective aluminum passivation for targeted immobilization of single DNA polymerase molecules in zero-mode waveguide nano structures. Proc. Natl. Acad. Sci. USA 105, 1176-1181 (2008), the disclosures of which are incorporated herein by reference in their entireties).

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

In embodiments involving sequencing on a substrate such as an array, paired end reads may be obtained on nucleic acid clusters. Methods for obtaining paired end reads are described in WO/07010252 and WO/07091077, each of which is incorporated herein by reference. Paired end sequencing facilitates reading both the forward and reverse template strands of each cluster during one paired-end read. Generally, template clusters are amplified on the surface of a substrate (e.g., a flow-cell) by bridge amplification and sequenced by paired primers sequentially. Upon amplification of the template strands, a bridged double stranded structure is produced. This can be treated to release a portion of one of the strands of each duplex from the surface. The single stranded nucleic acid is available for sequencing, primer hybridization and cycles of primer extension. After the first sequencing run, the ends of the first single stranded template can be hybridized to the immobilized primers remaining from the initial cluster amplification procedure. The immobilized primers can be extended using the hybridized first single strand as a template to resynthesize the original double stranded structure. The double stranded structure can be treated to remove at least a portion of the first template strand to leave the resynthesized strand immobilized in single stranded form. The resynthesized strand can be sequenced to determine a second read, whose location originates from the opposite end of the original template fragment obtained from the fragmentation process.

It will be appreciated that any of the above-described sequencing processes can be incorporated into the methods and/or compositions described herein. Furthermore, it will be appreciated that other known sequencing processes can be easily by implemented for use with the methods and/or compositions described herein.

Molecule Detection Systems

Also disclosed herein are molecule detection systems. The systems can include a solid support comprising molecules associated with a site on the solid support such that the molecules are detected in aggregate, wherein the molecules comprise at least two different types of molecules, and a detector configured to detect the molecules associated with the site.

As will be appreciated by those in the art, the number of possible solid supports is very large. Possible solid supports include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In some embodiments, the solid supports allow optical detection and do not themselves appreciably fluoresce.

In some embodiments, the configuration of the solid support is flat (planar), although as will be appreciated by those in the art, other configurations of solid supports may be used as well. For example, three dimensional configurations can be used. In some embodiments, the solid support can be hollow or porous. For example, beads having a mixture of molecules attached thereto can be embedded in a porous block of plastic that allows sample access to the beads and using a confocal microscope for detection. Similarly, beads may be placed on the inside surface of a tube, on the inner surface of a flow cell or on one of the lanes of a multi-lane flow chamber. In some such embodiments, the above configurations permit flow-through sample analysis and/or reduce the necessary sample volume. In other embodiments, the solid support comprises wells, such as microwells.

In some embodiments, fiber optic bundles can be used as substrates. In such embodiments, a mixture of molecules is associated with one end of the bundle. In particular, the a mixture of molecules can be associated with a fiber end, such as by direct chemical attachment, indirect attachment or other attachments or retention mechanisms. In some embodiments, one or more of the fibers have a well etched into an end, for example, as described in U.S. Pat. No. 7,622,294, the disclosure of which is incorporated herein by reference in its entirety. In such embodiments, a mixture of molecules can be attached at or within the well. In other embodiments, a mixture of molecules can be attached to a bead or other microparticle, which is then provided to the well. In a some embodiments, the bead is sized to be slightly smaller than the well. In other embodiments, multiple beads are included in the well. The beads may be of the same or different in size, shape, texture and/or the ability to generate a particular signal.

In some embodiments, silicon wafer solid supports are used. In some embodiments, the silicon may be doped as known in the art. In some embodiments, the substrate is in the shape of or is a microscope slide.

It will be appreciated that when beads or other particles are used as a solid support, such substrates can be used alone, used in groups of similar or different beads or particles, or used in connection with a second solid support. Further particular embodiments of bead substrates are described below.

In a preferred embodiment, the methods and compositions described herein utilize a robotic system. Many systems are generally directed to the use of 96 (or more) well microtiter plates, but as will be appreciated by those in the art, any number of different plates or configurations of solid support may be used. In addition, any or all of the steps outlined herein may be automated. Thus, for example, the systems may be completely or partially automated.

As will be appreciated by those in the art, there are a wide variety of components, one or more of which can be used, including but not limited to, one or more robotic arms; plate handlers for the positioning of microtiter plates or other solid supports; automated lid handlers to remove and replace lids to cover wells on non-cross contamination plates; a fluid handling device, such as one that includes tip assemblies for sample distribution; well loading blocks; cooled reagent racks; microtiter plate pipette positions (optionally cooled); stacking towers for plates and tips; one or more detectors for detecting signals; and computer systems.

Robotic systems can include automated fluid handling and/or particle-handing devices, including high throughput pipetting to perform steps involved in fluid dispensation, dispersion and/or removal. This includes liquid, and particle manipulations such as aspiration, dispensing, mixing, diluting, washing, accurate volumetric transfers; retrieving, and discarding of pipet tips; and repetitive pipetting of identical volumes for multiple deliveries from a single sample aspiration. In some embodiments, use of such systems can result in cross-contamination-free liquid and particle transfers.

In a preferred embodiment, platforms for multi-well plates, multi-tubes, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform can include a variable speed orbital shaker, and multi-position work decks for source samples, sample and reagent dilution, assay plates, sample and reagent reservoirs, pipette tips, and an active wash station.

In a preferred embodiment, interchangeable pipet heads (single or multi-channel) with single or multiple magnetic probes, affinity probes, or pipetters robotically manipulate the liquid and particles. Multi-well or multi-tube magnetic separators or platforms manipulate liquid and particles in single or multiple sample formats.

In some preferred embodiments, the instrumentation will include a detection system or detector. In some embodiments, the detection system provides a light source, or other energy source, configured to provide excitation energy to one or more sites on the solid support. In some embodiments, a CCD camera, CMOS or other signal detecting device is used to capture and detect, or otherwise record, signal data. In some embodiments, such data can be transformed into images or into other quantifiable formats using a computer. In some embodiments, one or more computers are involved in further displaying and/or analyzing the data. As will be discussed more fully below, in some embodiments, a computer or system of computers is used to analyze aggregate signal data in accordance with the methods for signal deconvolution described herein.

The flexible hardware and software configurations allow instrument adaptability for multiple applications. For example, in some embodiments, data processing modules or program modules allow creation, modification, and running of methods. In some embodiments, the system includes diagnostic modules that allow instrument alignment, correct connections, and refined motor operations. In addition, configurable tools, labware, and liquid and particle transfer patterns allow different applications to be performed. In some embodiments, robotic and computer interfaces allow communication between instruments.

In further embodiments, the molecule detection systems described herein include one or more databases that allow method and parameter storage. In some embodiments, signal data may be stored and retrieved from databases. In other embodiments, reference biosignatures can be stored in a database.

In some embodiments, the robotic workstation includes one or more heating or cooling components. Depending on the reactions and reagents, either cooling or heating may be required, which can be done using any number of known heating and cooling systems, including Peltier systems.

In a preferred embodiment, thermocycler and thermoregulating systems are used for stabilizing the temperature of the heat exchangers such as controlled blocks or platforms to provide accurate temperature control of incubating samples from 4° C. to 100° C.

In a preferred embodiment, the robotic apparatus includes a central processing unit (CPU) which communicates with a memory and a set of input/output devices (e.g., keyboard, mouse, monitor, printer, etc.) through a bus. The general interaction between a central processing unit, a memory, input/output devices, and a bus is known in the art. Thus, a variety of different procedures, depending on the experiments to be run, are stored in memory.

It will be appreciated that the molecule detection systems described herein need not be fully robotic. Rather, in some embodiments, only portions or parts of a robotic or automated system can be employed in the molecule detection systems described herein.

In some embodiments, the methods for aggregate signal deconvolution, such as those described in connection with the methods detection and/or identification methods set forth herein, can be implemented using one or more data processing modules or program modules. For example, a first data processing module can be configured to estimate the fraction of different types of molecules at the site or the amount of signal corresponding to different types of molecules at the site. In some embodiments, the same or a different module can include instructions for determining the variation associated one or both of the estimates.

In some embodiments, the systems can further include a second, or another, data processing module, for example a second data processing module, configured to utilize the variation associated with the estimate of one of the above-mentioned parameters to obtain an estimate for the other parameter. For example, the initial estimate for the fraction of different types of molecules at the site and the variation of that estimate can be used to calculate an estimate for the amount of signal corresponding to different types of molecules at the site. In some embodiments, this second data processor module can be combined with the first data processing or program module.

In other embodiments of the molecule detection systems described herein, the systems can further include a third, or another, data processing module configured to iteratively update the fraction estimate and signal estimate. In a preferred embodiment, the estimates are updated until they converge at or near a solution set.

In some embodiments, the systems are configured to detect and/or identify entire molecules. In some embodiments, the systems are configured to detect and/or identify portions of molecules. In a preferred embodiment, the systems are configured to detect and/or identify the complete nucleotide sequence of a nucleic acid or a portion of the complete nucleotide sequence of a nucleic acid, such as the nucleotide sequence of a target region of a nucleic acid.

In preferred embodiments, solid supports comprise sites at which molecules are associated and detected in aggregate. In some embodiments, when the solid support comprises one or more wells, the sites where molecules are associated can include wells. In some embodiments, the solid support is a bead and the site is the entire bead. In other embodiments, the solid support is a bead and the site is a portion or part of a bead. In some embodiments, the one or more beads are associated with a second solid support, such as wells of a microtiter or other multiwell plate, a lane or channel in a flow cell or a lane or channel in a multi-lane flow chamber.

In some embodiments of the systems described herein, the solid support is a plate, such as a picotiter plate, and the wells can further include one or more beads selected from the group consisting of beads having a nucleic acid associated therewith or attached thereto, beads having one or more enzymes associated therewith or attached thereto and blank beads or other beads having no nucleic acid or enzyme associated therewith or attached thereto. In preferred embodiments where beads having associated or attached enzymes are contemplated, the enzymes can comprise enzymes or enzymes systems useful for generating a detectable signal. For example, the signal can be colorimetric as is typical of the signal generating systems utilized with horseradish peroxidase. Other examples of enzymes or enzymes systems useful for generating signals include, but are not limited to, sulfurylase and luciferase. In some such embodiments, the enzyme system includes a sulfurylase enzyme and a luciferase enzyme associated with the same bead. In other such embodiments, the enzyme system includes a sulfuylase enzyme associated with a bead that is separate from the luciferase enzyme. In some embodiments, the well further includes beads having neither a nucleic acid nor an enzyme attached thereto.

Various numbers of molecules can be associated with the site. In some embodiments, about 1,000 to about 10,000 molecules are associated with the site. In some other embodiments, about 2,000 to about 8,000 molecules are attached to the site. In still some other embodiments, about 3,000 to about 6,000 molecules are attached to the site. In yet some other embodiments, about 4,000 to about 5,000 molecules are attached to the site.

In a preferred embodiment, the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In some embodiments of the molecule detection systems described herein, a site includes about 2 to about $10^{11}$ molecules, about 2 to about $10^{10}$ molecules, about 2 to about $10^9$ molecules, about 2 to about $10^8$ molecules, about 2 to about $10^7$ molecules, about 2 to about $10^6$ molecules, about 2 to about $10^5$ molecules, about 2 to about $10^4$ molecules. In other embodiments, a site includes about 10 to about $10^{11}$ molecules, about 10 to about $10^{10}$ molecules, about 10 to about $10^9$ molecules, about 10 to about $10^8$ molecules, about 10 to about $10^7$ molecules, about 10 to about $10^6$ molecules, about 10 to about $10^5$ molecules, about 10 to about $10^4$ molecules. In still other embodiments, the site includes about 50 to about $10^{11}$ molecules, about 50 to about $10^{10}$ molecules, about 50 to about $10^9$ molecules, about 50 to about $10^8$ molecules, about 50 to about $10^7$ molecules, about 50 to about $10^6$ molecules, about 50 to about $10^5$ molecules, about 50 to about $10^4$ molecules. In yet other embodiments, a site includes about 100 to about $10^{11}$ molecules, about 100 to about $10^{10}$ molecules, about 100 to about $10^9$ molecules, about 100 to about $10^8$ molecules, about 100 to about $10^7$ molecules, about 100 to about $10^6$ molecules, about 100 to about $10^5$ molecules, about 100 to about $10^4$ molecules. In any of the above-described embodiments of the molecule detection systems described herein, the molecules present at a site can be detected in aggregate. In some embodiments, the molecules are associated with the site. In other embodiments, the molecules are attached at the site. In certain embodiments, the molecules comprise nucleic acids.

Computer Implemented Embodiments

In some embodiments, one or more steps, such as those set forth herein, are carried out by a computer. In some embodiments, a computer is used to estimate the fraction of different types of molecules associated with a site on a solid support. In some embodiments, a computer is used to estimate the amount of signal corresponding to different types of molecules associated with the site. In some embodiments, a computer is used to calculate, or otherwise, obtain a signal estimate using the fraction estimate. In some embodiments, a computer is used to calculate, or otherwise obtain, a fraction estimate using the signal estimate. In some embodiments, a computer is used to iteratively update the fraction estimate and signal estimate until the estimates converge, thereby detecting molecules associated with the site on the solid support. As will be appreciated, the fraction estimate and/or signal estimate can be obtained by a variety of mathematical methods known in the art including, but not limited to, a numerical optimization algorithm. In preferred embodiments the numerical optimization algorithm is based on an iterative map search or Fienup's iteration map.

Exemplary computer systems, which are useful in implementing the methods and/or compositions described herein, include, but are not limited to, personal computer systems, such as those based on Intel®, IBM®, or Motorola® microprocessors; or work stations such as a SPARC workstation or UNIX workstation. Useful systems include those using the Microsoft Windows, UNIX or LINUX operating system. The systems and methods described herein can also be implemented to run on client-server systems or wide-area networks such as the internet.

A computer system useful in implementing the methods and/or compositions described herein can be configured to operate as either a client or server and can include one or more processors which are coupled to a random access memory (RAM). Implementation of embodiments of the methods and/or compositions described herein is not limited to any particular environment or device configuration. The embodiments of the present invention may be implemented in any type of computer system or processing environment capable of supporting the methodologies that are set forth herein. In particular embodiments, algorithms can be written in MATLAB, C or C++, or other computer languages known in the art.

In some embodiments described herein, a computer can be used in the acquisition and storage of data relating to the compositions and methods described herein. For example, in some embodiments, the computer can be programmed, or otherwise instructed, to sequence data and/or other relevant information to a user, another computer, a database or a network. In additional embodiments, the computer can also be programmed, or otherwise instructed, to receive relevant information from a user, another computer, a database or a network. Such information can include data, such as signals or images, obtained from a sequencing method, one or more reference sequences, characteristics of an organism of interest or the like.

Identification of Biosignatures and Other Applications

Methods, systems and compositions described herein are useful tools in obtaining the biosignature for a population of molecules, such as nucleic acids, associated with a site on a solid support. In some embodiments, molecules associated at a site on a solid support are detected in aggregate by detecting a signal corresponding to the aggregate of molecules. The aggregate signal can then be deconvoluted in accordance with one or more of the methods described herein in order to obtain a biosignature for a population or a subpopulation of molecules present at the site.

In some embodiments, a solid support having molecules associated therewith is provided. In such embodiments, a user then determines a biosignature for one or more populations or subpopulations of molecules associated with one or more sites on the solid support. Alternatively, in some embodiments, the user of the solid support, associates molecules from one or more samples with one or more sites on the solid support. In a preferred embodiment, a population of molecules, which comprises at least two different types of molecules, and which was obtained from a sample, is associated with a site on a solid support. In some embodiments, the molecules of the sample are tagged prior to or subsequent to associating them with the solid support. In some such embodiments, the tags are utilized to identify the subject or source from which the sample was obtained. In some embodiments, the samples are obtained from a plurality of subjects or sources.

The sequencing and/or biosignature information that can be obtained using the methods described herein can be used in a variety of applications involved in, but not limited to, genotyping, expression profiling, identifying alternative splicing, genome mapping, amplicon sequencing, methylation detection, metagenomics, SNP detection, pathogen infection detection, treatment outcome prediction, pollution detection, determining disease progression state, and environmental monitoring.

In one example, the methods described herein can deconvolute the aggregate signal generated by multiple types of molecules associated with a site of a solid support, thereby permitting identification of the different types of molecules present at the site. In some embodiments, the different types of molecules include alleles of a genetic locus from a polyploid organism, including, but not limited to, a diploid organism, such as a mammal (for example, rats, mice and humans); a triploid organism, such as seedless watermelons; a tetraploid organism, such as Salmonidae fish; a pentaploid organism, such as Kenai Birch, and a hexaploid organism, such as wheat and kiwifruit. In some embodiments, the different types of molecule components include alternative splicing forms of a nucleic acid. In some embodiments, the different types of molecules include nucleic acids or proteins from variants of a particular organism, including, but not limited to, a virus (for example, HIV, HCV and HBV), a bacterium (for example, a pathogenic bacterium such as $E.$ $coli$ O:157), and/or a eukaryotic cell. In some embodiments, the variation(s) between the different types of molecular components include a mutation, a polymorphism, an insertion, a deletion, a substitution, a simple tandem repeat polymorphism, or a single nucleotide polymorphism (SNP).

In one example, the methods described herein can provide a biosignature for populations of molecules or subpopulations of molecules in a sample. Accordingly, in some embodiments, the complete sequence of each type of molecule of the sample need not be determined and, instead, the sequence of portions of all or some of the different types of molecules of the population or subpopulation can be determined and used.

In some embodiments, the sample is an environmental sample from any environmental source. In some embodiments, the environmental sample is obtained from naturally occurring or artificial sources. In some embodiments, the sample is obtained from the atmosphere, water systems, soil or any other source of interest. In other more particular embodiments, the environmental samples can be obtained from, for example, atmospheric pathogen collection systems, sub-surface sediments, groundwater, ancient water deep within the ground, plant root-soil interface of grassland, coastal water and sewage treatment plants.

In some embodiments, the sample can be any kind of investigational, clinical or medical sample. In some examples, samples can be obtained from a subject, such as from the blood, the lungs or the gut of mammals. In some embodiments, the sample is a biological sample obtained from a subject suspected or is suffering from a certain disease. In some embodiments, the molecules comprise a marker from a pathogen. Non-limiting examples of pathogen include a virus, a bacterium, and a eukaryotic cell, such as a tumorogenic or cancer cell.

In some embodiments, the biosignature obtained for all of the molecules in a sample or a subpopulation of molecules in the sample can be compared to a reference biosignature. In some embodiments, the similarities and/or differences between the biosignature obtained for the sample and the reference biosignature can be used to identify an organism or pathogen, predict a treatment outcome for a patient, estimate disease progression state, estimate extent of pollution in certain environment.

Bead Mixtures

Some embodiments of the compositions described herein relate to mixtures of beads. In some embodiments, the mixtures of beads comprise a plurality of beads, wherein each bead of the plurality of beads comprises a first subpopulation and a second subpopulation of nucleic acids. In certain embodiments, the first subpopulation and the second subpopulation of nucleic acids are associated with the bead such that they are detected in aggregate. In preferred embodiments, the nucleic acids of the first subpopulation each comprise an identical target region and the nucleic acids of the second subpopulation each comprise an identical region that is a variant of the target region.

In some embodiments of the above-described mixture of beads, the nucleic acids are attached to each bead of the plurality of beads.

In some embodiments, the mixture of beads is distributed on the substrate. In other embodiments, a plurality of beads having beads comprising both the first subpopulation and a second subpopulation of nucleic acids is distributed on a substrate. In some embodiments, the distribution of beads on the substrate is a random distribution. In other embodiments, the substrate includes wells and the beads are distributed in the wells. In yet other embodiments, wells of the substrate further include beads having an enzyme attached thereto. In preferred embodiments, the enzyme can include sulfurylase, luciferase or a combination of sulfurylase and luciferase. In some embodiments, wells of the substrate further include beads having neither a nucleic acid nor enzyme attached thereto.

Solid Supports Having a Reduced Number of Molecules Associated Therewith

Some embodiments described herein relate to beads and/or other solid supports that are useful for attaching mixtures of molecules at a reduced number. In certain preferred embodiments of the methods and systems described herein, solid supports having a reduced number of molecules associated therewith are desirable for certain statistical analyses. The embodiments below describe compositions having molecules associated therewith at reduced numbers. Additionally, various methods for associating molecules with a site on a solid supports at reduced numbers are described.

In preferred embodiments, of the above-described solid support the initial number of molecules associated with a site ranges from about 10 to about 1000 molecules. In another preferred embodiment, about 10 to about 500 molecules are initially associated with the site. In yet another preferred embodiment, about 10 to about 100 molecules are initially associated with the site.

In some embodiments where the molecules are nucleic acids, the solid support further comprises one or more capture probes and/or one or more primers complementary to a portion of one or more of the molecules associated with the site on the solid support.

In some embodiments, the number of capture probes associated with the site on the solid support can be reduced by reducing the concentration of capture probes used in the association process. Although this method produces solid supports with sites that have a low or considerably reduced number of capture probes associated therewith, the number of sites having no capture probes is also increased.

In other embodiments, the number of capture probes associated with the site on the solid support can be reduced by introducing competitor molecules, such as a complementary oligonucleotides. The complementary oligonucleotides are hybridized with capture probes at the site such that at least about 10%, at least about 20%, at least about 30%, at least about 40%, at least about 50%, at least about 60%, at least about 70%, at least about 80%, at least about 90%, at least about 95%, at least about 99%, at least about 99.9% of the capture probes are hybridized with competitor oligonucleotides. Subsequently, nucleic acids of interest can be hybridized with the reduced number of capture probes so as to produce a solid support having a reduced number of nucleic acids of interest associated therewith.

In some embodiments, the above methods are applied to beads. In some such embodiments, the resulting bead composition comprises a first subpopulation of capture nucleic acids having a competitor molecule hybridized thereto and a second subpopulation of capture nucleic acids comprising a region that permits hybridization of a complementary molecule.

In still other embodiments, the number of capture probes associated with the site on the solid support can be reduced by first amplifying nucleic acids of interest to produce a population of amplified nucleic acids that include a region intended to be complementary to a capture probe (a tag region), wherein the tag region is degenerate among nucleic acids within the population. As such, only a portion of the amplified population of nucleic acids will hybridize with capture probes at the site on the solid support, thereby producing sites having a reduced number of nucleic acids associated therewith. The number of nucleic acids that hybridize with capture probes can be adjusted up or down by adjusting the amount of degeneracy introduced into the tag region and/or adjusting the stringency of hybridization.

In some embodiments the above methods are applied to beads. In some such embodiments, the resulting bead composition comprises capture nucleic acids hybridized with an amplified nucleic acid comprising a degenerate tag. In some such embodiments, the degenerate tag is hybridized to a capture nucleic acid.

In some embodiments of the above-described bead compositions, beads are distributed, or otherwise present, in a channel of a substrate. In other embodiments, the bead is present in a well of a multiwell substrate. In a preferred embodiment, the well is configured to hold a single bead having the amplified nucleic acid hybridized thereto. In even more preferred embodiments, the well comprises a single bead having the amplified nucleic acid hybridized thereto as well as a plurality of beads that are smaller in size than the single bead. In especially preferred embodiments, the wells are configured to accommodate a plurality of beads that are smaller in size than the single bead. In even more preferred embodiments, a portion of the small bead population in the well comprises beads having one or more enzymes attached. In even more preferred embodiments, a portion of the small bead population in the well comprises blank beads or beads having neither a nucleic acid nor protein attached thereto.

In some embodiments of the above-described solid supports, the population of nucleic acids includes alleles of a genetic locus from a polyploid organism. In other embodiments, the population of nucleic acids includes alternative splicing forms of a nucleic acid. In yet other embodiments, the population of nucleic acids includes alleles of a genetic locus from a diploid organism.

In any of the above-described embodiments of beads, mixtures of beads and/or other solid supports described herein that comprise nucleic acids, a population of nucleic acids or a subpopulation of nucleic acids present on the bead, can be detected in aggregate. In some embodiments, the nucleic acids are associated with the bead. In other embodiments, the nucleic acids are attached at the bead.

EXAMPLES

Embodiments of the present disclosure are disclosed in further detail in the following examples, which are not in any way intended to limit the present disclosure.

Example 1

Detecting Molecules in Aggregate

In some embodiments, two different types of molecules, for example allele 1 and allele 2, associated with a site on a solid support are detected in aggregate. The aggregate signals observed, i.e., the observations (O), are generated from a mixture of allele 1 and allele 2. As such, the signal observed is the combined signal from a mixture of types of molecules (templates) $t_1$ and $t_2$ with the weighted sum of signal from pure templates. The observations (O) are arranged in a column matrix with notation: O=tf, where "t" represents the template matrix having non-negative, integer entries reflecting the amount of signal generated from each type of molecule and "f", which represents the fraction matrix corresponding the template matrix, is constrained such that all columns that sum to 1.

With observations O, values for t and f can be calculated by first guessing the fraction matrix and using the variation associated with that guess to calculate an estimate for the template matrix using a least squares estimation as follows:

$$o = tf$$

$$t_{new} = of^T(ff^T)^{-1}$$

Subsequent to calculating the estimate, elements of t are set to zero if negative and rounded to integers if not negative.

Alternatively, the methods described herein can be used to first estimate fractions starting from a template matrix. Such a process is similar to that indicated above, in that the template matrix is first guessed. The variation associated with that guess is used to calculate an estimate for the fraction matrix using the following least squares estimation:

$$O = tf$$

$$f_{new} = (t^T t)^{-1} t^T O$$

Subsequent to calculating the estimate, elements of f are set to zero if negative, and each column is divided by its sum.

Now that starting estimates have been obtained for each matrix, these estimates can be updated until convergence on a solution set is reached. Here a Fienup algorithm is used to implement the updating steps using a personal computer as follows:

$x = (t, f)$ with the convention that $P_A(x)$ updates only the template t, and $P_B(x)$ updates only the fractions f. The Fienup iteration is defined as:

$$x \to x + P_A(2P_B(x) - x) - P_B(x)$$

The update is iterated until convergence and a solution set for the template and fraction matrices is obtained.

Example 2

Detecting Molecules in Aggregate in Single Flow Systems

In some embodiments, only one flow varies and only one signal (O) is observed. In such cases, matrix methods are not employed. In such situations, O can be modeled as:

$$O = IL_A X + IL_B(N - X), \text{ where}$$

$L_A$ is the length for allele A
$L_B$ is the length for allele B
I is the intensity per molecule
N is the number of molecules associated on the site, and
X is the number of molecules of allele A on the site Under this model, an estimate of O/I (the observation divided by the intensity factor) and the variance of that estimate can be set forth as follows:

$$E\left[\frac{O}{I}\right] = L_A N p + L_B N(1 - p)$$

$$\text{Var}\left[\frac{O}{I}\right] = N p(1 - p)(L_A - L_B)^2$$

where p is the probability that a molecule at the site includes allele A.

Here, the variance of the observation depends on the difference between allele nucleotide run lengths, which allows inference of the combination of alleles by statistical analysis of the observation for the site.

Example 3

Computer-Simulations

The following simulations were run to demonstrate that the methods described herein were robust enough to deconvolve mixed signals produced sets of molecules, having different types of variant regions. In order to generate molecule pairs appropriate for such simulations, a first nucleic acid sequence was generated at random. Next a mutation type was chosen at random from one of the following mutation types: (1) nucleotide substitution; (2) nucleotide insertion; (3) nucleotide deletion; and (4) random nucleotide sequence.

In cases where a nucleotide substitution was selected, a small random number was generated and was used to determine the number of bases replaced with different bases to generate a second sequence from the first. The second sequence was employed as a nucleotide substitution variant of the first nucleotide sequence.

In cases where a nucleotide deletion was selected, a short nucleotide sequence was deleted from the first sequence, and then, the same number of random nucleotides were appended to the sequence in order to generate a second sequence having the same length as the first sequence. The second sequence was employed as a nucleotide sequence deletion variant of the first nucleotide sequence.

In cases where a nucleotide insertion was selected, a short nucleotide sequence was introduced into the first sequence, and then, the same number of nucleotides were removed from the sequence in order to generate a second sequence having the same length as the first sequence. The second sequence was employed as a nucleotide sequence insertion variant of the first nucleotide sequence.

In cases where the second sequence was random as compared to the first sequence, the second sequence was generated at random, independently from the first Multiple sequence pairs were generated for each of the four categories above. The sequences in each pair were from approximately 75 to approximately 200 nucleotides in length. For each sequence pair, sequencing flows were simulated and several thousand random proportions were chosen according the binomial distribution. A number of simulated mixed flows were generated for various proportions of the two sequences, forming the observation matrix. This observation matrix was used as input to the algorithms described in Examples 1 or 2 depending on the type of sequencing run that was simulated. The optimization was run and the resulting output sequences were compared to the input sequences for the final evaluation.

In nearly all of the simulations, convergence was reached in less than 300 iterations. The output sequences closely matched the input sequences having an error rate on the order of $10^{-11}$.

Example 4

Detection of HIV Variants in a Patient

DNA is extracted from the blood sample obtained from an HIV patient. An HIV marker gene, such as gp41 and p24, is amplified from the HIV's patient's DNA and attached to beads for sequencing. The methods described herein are used to detect whether there are at least two different variants of the HIV marker gene present in the patient's DNA sample. The presence of genetic variation(s) in the HIV marker gene can be used to indicate the progression of HIV infection in the patient, determine the effectiveness of prior HIV treatment, and/or improve prognosis to the patient.

Example 5

Quality Control of Wastewater Treatment Plant

DNA is extracted from a water sample obtained from a wastewater treatment plant. Primers specific for amplifying the 16S rRNA genes from bacteria that are commonly found in human feces and sewage samples are used to amplify 16S rRNA genes from the DNA obtained from the water sample and attached to beads for sequencing. The methods described herein are used to detect the presence of one or more bacteria of interest, such as the presence of different types of fecal coliforms. The presence of any bacteria of interest is an indication of fecal contamination at the wastewater treatment plant.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A system of detecting molecules, said system comprising:
    (a) a solid support comprising molecules associated with a site on the solid support, wherein the site comprises at least two different types of molecules comprising nucleic acids;
    (b) a detector configured to detect at least one signal corresponding to aggregates of molecules comprising nucleic acids at the site;
    (c) a first data processing module configured to provide an initial estimate of the amount of signal corresponding to each of the at least two different types of molecules comprising nucleic acids at the site;
    (d) a second data processing module configured to calculate the amount of signal corresponding to each of the at least two different types of molecules comprising nucleic acids at the site using the initial estimate, thereby obtaining a signal estimate; and
    (e) a third data processing module configured to iteratively update the initial estimate until the signal estimates converge, thereby detecting molecules associated with the site.

2. The system of claim 1, wherein the solid support comprises glass, plastic, carbon, metal, a resin or silicon.

3. The system of claim 2, wherein the plastic is selected from the group consisting of acrylics, polystyrenes, copolymers of styrene, polypropylene, polyethylene, polybutylene, polyurethanes, and Teflon.

4. The system of claim 1, wherein the solid support is a planar solid support.

5. The system of claim 1, wherein the solid support comprises a flow-cell.

6. The system of claim 1, wherein the solid support comprises wells.

7. The system of claim 1, wherein the solid support comprises beads attached to the at least two different types of molecules comprising nucleic acids.

8. The system of claim 1, further comprising a robotic automation system.

9. The system of claim 8, wherein the robotic automation system comprises a device selected from the group consisting of a robotic arm, a plate handler, an automated lid handler, a fluid handling device, a well loading block, a heating/cooling system, and a reagent rack.

10. The system of claim 1, wherein the detector comprises an energy source configured to provide excitation energy to one or more sites on the solid support.

11. The system of claim 1, wherein the detector further comprises a CCD camera, or CMOS.

12. The system of claim 1, wherein the first data processing module is configured to perform a principal component analysis (PCA) to determine the initial estimate of the amount of signal corresponding to each of the at least two different types of molecules comprising nucleic acids at the site.

13. The system of claim 1, wherein the third data processing module is configured to perform a numerical optimization algorithm.

14. The system of claim 13, wherein the numerical optimization algorithm is based on an iterative map search or Fienup's iteration map.

15. The system of claim 1, wherein a data processing module is configured to obtain sequence data for one or more of the at least two different molecules comprising nucleic acids.

16. The system of claim 15, wherein sequence data is obtained by a sequencing-by-synthesis process.

17. The system of claim 1, wherein the molecule detection system is configured to identify the nucleotide sequence of a target region of a nucleic acid.

18. The system of claim 1, wherein the nucleic acids comprise a first subpopulation of nucleic acids having first target regions and a second subpopulation of nucleic acids having second target regions, wherein the first target regions are identical to one another and the second target regions are identical to one another, and the second target regions are a variant of the first target regions.

19. The system of claim 18, wherein the nucleotide sequence of said target region of the nucleic acids of the first subpopulation has at least 3 nucleotides that are different as compared to the nucleotide sequence of said variant of the target region of the nucleic acids of the second subpopulation.

20. The system of claim 1, wherein the nucleic acids comprise alleles of a genetic locus.

21. A system of detecting molecules, said system comprising:
    (a) a solid support comprising molecules associated with a site on the solid support, wherein the site comprises at least two different types of molecules, wherein the at least two different types of molecules comprise nucleic acids;
    (b) a detector configured to detect at least one signal corresponding to aggregates of molecules comprising nucleic acids at the site;
    (c) a first data processing module configured to provide an initial estimate of the fraction of signal corresponding to each of the at least two different types of molecules comprising nucleic acids at the site;
    (d) a second data processing module configured to calculate the fraction of signal corresponding to each of the at least two different types of molecules comprising nucleic acids at the site using the initial estimate, thereby obtaining a fraction estimate; and (e) a third data processing module configured to iteratively update the initial estimate until the fraction estimates converge, thereby detecting molecules associated with the site.

22. A system for detecting molecules, comprising:

(a) a solid support comprising molecules associated with a site on the solid support such that the molecules are detected in aggregate during a detection step, wherein the site comprises at least two different types of molecules, wherein the molecules comprise nucleic acids;

(b) means for detecting a signal corresponding to the aggregate of molecules comprising nucleic acids at the site;

(c) means for providing an initial estimate of the amount of signal corresponding to each of the at least two different types of molecules comprising nucleic acids at the site;

(d) means for calculating the amount of signal corresponding to each of the at least two different types of molecules comprising nucleic acids at the site using the initial estimate, thereby obtaining a signal estimate; and (e) means for iteratively updating the initial estimate until the signal estimates converge, thereby detecting molecules associated with the site.

* * * * *